United States Patent [19]

D'Cruz et al.

[11] Patent Number: 6,051,603
[45] Date of Patent: Apr. 18, 2000

[54] VANADIUM (IV) METALLOCENE COMPLEXES HAVING SPERM MOTILITY INHIBITING ACTIVITY

[75] Inventors: Osmond D'Cruz, Maplewood; Phalguni Ghosh, St. Anthony; Fatih M. Uckun, White Bear Lake, all of Minn.

[73] Assignee: Wayne Hughes Institute, St. Paul, Minn.

[21] Appl. No.: 09/008,898

[22] Filed: Jan. 20, 1998

[51] Int. Cl.$^7$ .................................................... A61K 31/28
[52] U.S. Cl. ................................................................ 514/492
[58] Field of Search ................................................ 514/492

[56] References Cited

U.S. PATENT DOCUMENTS

| | | |
|---|---|---|
| 4,297,341 | 10/1981 | Waller et al. . |
| 4,322,399 | 3/1982 | Ahmad et al. . |
| 4,368,186 | 1/1983 | Vickery et al. . |
| 4,432,967 | 2/1984 | Szymanski . |
| 4,588,581 | 5/1986 | Schmolka . |
| 4,613,497 | 9/1986 | Chavkin . |
| 4,707,362 | 11/1987 | Nuwayser . |
| 4,795,425 | 1/1989 | Pugh . |
| 4,917,901 | 4/1990 | Bourbon et al. . |
| 4,999,342 | 3/1991 | Ahmad et al. . |
| 5,013,544 | 5/1991 | Chantler et al. . |
| 5,069,906 | 12/1991 | Cohen et al. . |
| 5,387,611 | 2/1995 | Rubinstein . |
| 5,407,919 | 4/1995 | Brode et al. . |
| 5,512,289 | 4/1996 | Tseng et al. . |
| 5,595,980 | 1/1997 | Brode et al. . |

OTHER PUBLICATIONS

D'Cruz, O. et al., "Spermicidal activity of metallocene complexes containing vanadium(IV) in humans", *Chemical Abstracts*, vol. 129, Abstract No. 76657x, 1 page, 1998.

D'Cruz, O. et al., "Spermicidal activity of oxovanadium(IV) complexes of 1,10–phenanthroline, 2,2'–bipyridyl, 5'–bromo–2'–hydroxyacetophenone and derivatives in humans", *Chemical Abstracts*, vol. 13, Abstract No. 262258, 1 page (1999).

Aitken, et al., 1989, *Biol Reprod*, 40:183–197 "Generation of Reactive Oxygen Species, Lipid Peroxidation and Human Sperm Function".

Aitken, et al., 1993, *J Reprod Fertil*, 97:441–450 "Use of a Xanthine Oxidase Free Radical Generating System to Investigate the Cytotoxic Effects of Reactive Oxygen Species on Human Spermatozoa".

Aitken, et al., 1994, *Bio Essays*, 16:259–267 "Reactive Oxygen Species Generation and Human Spermatozoa: The Balance of Benefit and Risk".

Alvarez, et al., 1987, *J Androl*, 8:338–348 "Spontaneous Lipid Peroxidation and Production of Hydrogen Peroxide and Superoxide in Human Spermatozoa".

Biggers, et al., 1971, *Methods in Mammalian Embryology*, Daniel, JC Jr. (ed.), San Francisco: Freeman, pp. 86–116 "The Culture of Mouse Embryos in vitro".

Bourinbaiar, et al., 1994, *Life Sci*, 54:PL 5–9 "Anti–HIV Effects of Gramicidin in vitro: Potential for Spermicidal Use".

Burkman, L.J., 1991, *Fertil Steril*, 55:363–371 "Discrimination Between Nonhyperactivated and Classical Hyperactivated Motility Patterns in Human Spermatozoa Using Computerized Analysis".

Butler A., et al., 1989, *Inorganica Chimica Acta*, 163:1–3 "Reactivation of Vanadate–Inhibited Enzymes with Deferoxamine B, a Vanadium (V) Chelator".

Byczkowski, et al., 1988, *Bull Environ Contam Toxicol*, 41:696–703 "Vanadium–Mediated Lipid Peroxidation in Microsomes from Human Term Placenta".

Carmichael A.J., 1990, *FEBS Lett*, 261:165–170 "Vanadyl–Induced Fenton Like Reaction in RNA: an ESR and Spin Trapping Study".

D'Cruz, et al., 1995, *Biol Reprod*, 53:1118–1130 "$\beta_2$–Integrin (CD11b/CD18) is the Primary Adhesive Glycoprotein Complex Involved in Neutrophil–Mediated Immune Injury to Human Sperm".

Dorer, et al., 1997, *Collect Czech Chem Comm*, 62:265–277 "ansa–Vanadocene Complexes–Syntheses, Structures and Ligand Exchange Reactions".

Doyle, et al., 1968, *Inorg Chem*, 7:2479–2484 "Pseudohalide and Chelate Complexes of Bis(cyclopentadienyl)vanadium(IV)".

Erlandsen, et al., 1989, *Scanning*, 11:169–175 "Membrane Fixation for High–Resolution Low–Voltage SEM: Studies on Giardia, Rat Spermatozoa, and Mouse Macrophages".

Gavrieli, et al., 1992, *J Cell Biol*, 119:493–501 "Identification of Programmed Cell Death in situ via Specific Labeling of Nuclear DNA Fragmentation".

Gibbons, et al., 1978, *Proc Natl Acad Sci USA*, 75:2220–2224 "Potent Inhibition of Dynein Adenosinetriphosphatase and of the Motility of Cilia and Sperma Flagella by Vanadate".

Jones, et al., 1979, *Fertil Steril*, 31:531–537 "Peroxidative Breakdown of Phospholipids in Human Spermatozoa: Spermicidal Effects of Fatty Acid Peroxides and Protective Action of Seminal Plasma".

Kopf–Maier, et al., 1981, *Eur J Cancer*, 17:665–669 "Tumor Inhibition by Metallocenes: Activity Against Leukemias and Detection of the Systematic Effect".

(List continued on next page.)

*Primary Examiner*—M. Mozie
*Attorney, Agent, or Firm*—Merchant & Gould P.C.

[57] ABSTRACT

Novel spermicidal compounds which are organometallic cyclopentadienyl metal complexes, particularly vanadium IV complexes, are described including corresponding contraceptive and therapeutic compositions and method for providing contraception and selective killing of testicular germ cells. Included among the vanadium complexes are vanadocene dichloride, vanadocene dibromide, bis (methyl cyclopentadienyl) vanadium dichloride, vanadocene diiodide, vanadocene di-pseudohalides, and others. Most active found was vanadocene diselenocyanate.

8 Claims, 15 Drawing Sheets

OTHER PUBLICATIONS

Kopf–Maier, et al., 1983, *Chem Biol Interactions*, 44:317–328 "Tumor Inhibition by Metallocenes: Ultrastructural Localization of Titanium and Vanadium in Treated Tumor Cells by Electron Energy Loss Spectroscopy".

Kopf–Maier, et al., 1981, *Cancer Chemother Pharmacol*, 5:237–241 "In vitro Cell Growth Inhibition by Metallocene Dichlorides".

Kopf–Maier, et al., 1983, *J Cancer Res Clin Oncol*, 106:44–52 "Induction of Cell Arrest at $G_1/S$ and in $G_2$ After Treatment of Ehrlich Ascites Tumor Cells with Metallocene Dichlorides and cis–Platinum in vitro".

Kopf–Maier, et al., 1988, *Structure and Bonding*, 70:103–185 "Transition and Main–Group Metal Cyclopentadienyl Complexes: Preclinical Studies on a Series of Antitumor Agents of Different Structural Type".

Kopf–Maier, et al., 1984, *Virchows Arch [Cell Pathol]*, 47:107–122 "Cytologic Observations on the Effects of Metallocene Dichlorides on Human Fibroblasts Cultivated in vitro".

Kopf–Maier, et al., 1993, In: Kepper BK (ed.), *Metal Complexes in Cancer Chemotherapy*, New York: VCH Publishers, pp. 259–296 "Antitumor bis(cyclopentadienyl) Metal Complexes".

Kuo et al., 1996, In: Sigel H.(ed.), *Metal Ions in Biological Systems*, pp. 53–85 "Metallocene Interactions with DNA and DNA–Processing Enzymes".

Macara I.G., 1980, Trends Biochem Sci, 5:92–94 "Vanadium—An Element in Search of a Role".

Martin, et al., 1995, *J Exp Med*, 182:1545–1556 "Early Redistribution of Plasma Membrane Phosphotidylserine is a General Feature of Apoptosis Regardless of the Initiating Stimulus: Inhibition by Overexpression of Bcl–2 and Abl".

McLaughlin, et al., 1990, *J Am Chem Soc*, 112:8949–8952 "DNA–Metal Binding by Antitumor–Active Metallocene Dichlorides from Inductively Coupled Plasma Spectroscopy Analysis: Titanocene Dichloride Forms $DNA-Cp_2$ Ti or DNA–CpTi Adducts Depending on pH".

Moebus, et al., 1997, *Anticancer Res*, 17:615–822 "Antitumor Activity of New Organometallic Compounds in Human Ovarian Cancer Cell Lines and Comparison to Platin Derivatives".

Moran, et al., 1985, *J Organometallic Chemistry*, 291:311–319 "Synthesis and Characterization of Halogen and Pseudohalogen Derivatives of Substituted Vanadocenes".

Murthy, et al., 1988, *Inorg Chemica Acta*, 152:117–124 "Antitumor and Toxicologic Properties of the Organometallic Anticancer Agent Vanadocene Dichloride".

Niruthisard, et al., 1991, *Sex Transm Dis*, 18:176–179 "The Effects of Frequent Nonoxynol–9 Use on the Vaginal and Cervical Mucosa".

Ozawa, et al., 1989, *Chem Pharma Bull*, 37:1407–1409 "ESR Evidence for the Formation of Hydroxyl Radicals During the Reaction of Vanadyl Ions with Hydrogen Peroxide".

Petersen, et al., 1975, *J Am Chem Soc*, 97:6422–6433 "Synthesis and Structural Characterization by X–ray Diffraction and Electron Paramagnetic Resonance Single–Crystal Techniques of $V(\eta^5-C_5H_4CH_3)_2Cl_2$. A Study of the Spatial Distribution of the Unpaired Electron in a $V(\eta_5-C_5H_5)_2L_2$–type Complex".

Rehder, D., 1991, *Angew Chem Int Ed Engl*, 30:148–167 "The Bioinorganic Chemistry of Vanadium".

Roddy, et al., 1993, *Int J STD AIDS*, 4:165–170 "A Dosing of Nonoxynol–9 and Genital Irritation".

Sakurai, et al., 1992, *Biochem Biophys Res Commun*, 189:1090–1095 "DNA Cleavage by Hydroxyl Radicals Generated in a Vanadyl Ion–Hydrogen Peroxide System".

Sakurai, et al., 1995, *Biochem Biophys Res Commun*, 206:133–137 "Mechanism for a New Antitumor Vanadium Complex Hydroxyl Radical–Dependent DNA–Cleavage by 1,10–Phenanthroline–vanadyl Complex in the Presence of Hydrogen Peroxide".

Shi, et al., 1996, *Ann Clin Lab Sci*, 26:39–49 "Vanadium(IV) Causes 2'–Deoxyguanosine Hydroxylation and Deoxyribonucleic Acid Damage Via Free Radical Reactions".

Stoffel, et al., *Molecular Reprod Develop* 1993; 34:175–182 "Improved Preservation of Rat Epididymal Sperm for High–Resolution Low–Voltage Scanning Electron Microscopy (HR–LVSEM)".

Thewalt, et al., 1995, *Transition Metal Chem*, 10:393–395 "The Crystal and Molecular Structure of Acetonitrilechlorodicyclopentadienyltitanium Tetrachloroferrate (III). Some Mössbauer and X–Ray Photoelectron Spectroscopic Data".

Toney, et al., 1985, *J Am Chem Soc*, 107:947–953 "Hydrolysis Chemistry of the Metallocene Dichlorides $M(\eta^5-C_5H_5)_2Cl_2$, M=Ti, V, Zr. Aqueous Kinetics, Equilibria, and Mechanistic Implications for a New Class of Antitumor Agents".

Tryphonas, et al., 1984, *Toxicol* Lett, 20:289–295 "Morphologic Evidence for Vaginal Toxicity of Delfen Contraceptive Cream in the Rat".

Tryphonas, et al., 1986, *Toxicol*, 39:177–186 "Effects of the Spermicide Nonoxynol–9 on the Pregnant Uterus and the Conceptus of Rat".

Vermes, et al., 1995, *J Immunol Meth*, 184:39–51 "A Novel Assay for Apoptosis. Flow Cytometric Detection of Phosphatidylserine Expression on Early Apoptotic Cells Using Fluorescein Labelled Annexin V".

Wilborn, et al., 1983, *Fertil Steril*, 39:717–719 "Scanning Electron Microscopy of Human spermatozoa After Incubation with the Spermicide Nonoxynol–9".

Wilkinson, et al., 1954, *J Am Chem Soc*, 76:4281–4284 "Bis–cyclopentadienyl Compounds of Ti, Zr, V, Nb, and Ta".

Wilkinson, G., 1982, *Comprehensive Organometallic Chemistry*, New York, Pergamon, 3:554–646 "Zirconium and Hafnium: Introduction".

Younes, et al., 1991, *Toxicology*, 66:63–74 "Vanadate–Induced Toxicity Towards Isolated Perfused Rat Livers: The Role of Lipid Peroxidation".

A. Metallocene dichlorides:  = Cyclopentadiene (Cp)
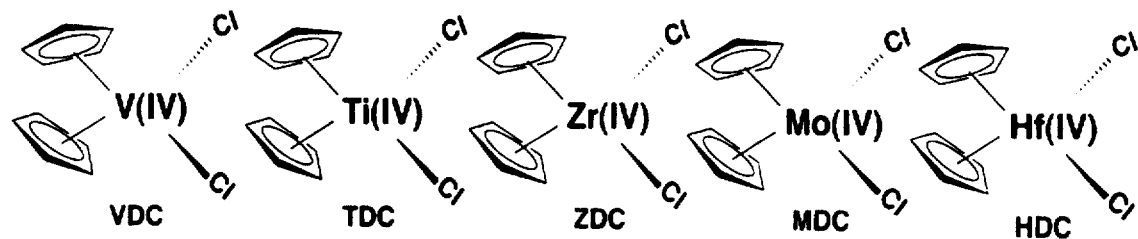
B. Vanadocene dihalides:
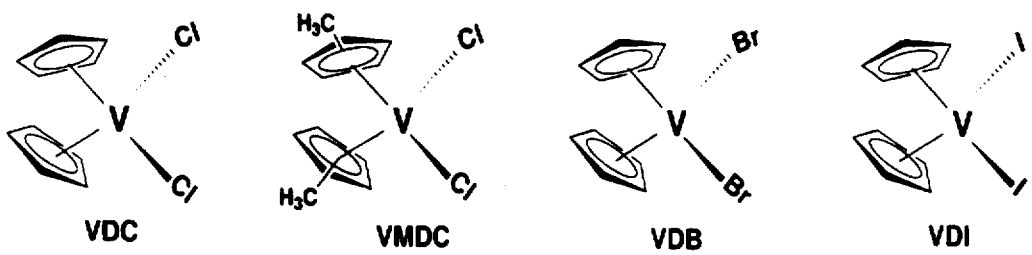
C. Vanadocene di-pseudohalides:
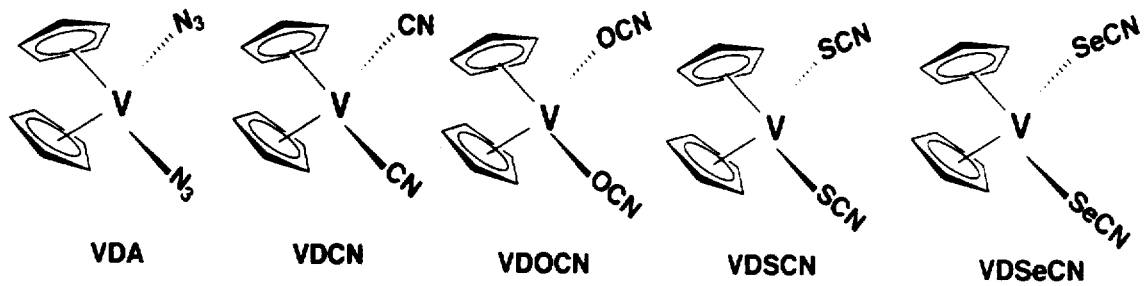
D. Vanadocene disubstituted derivatives:
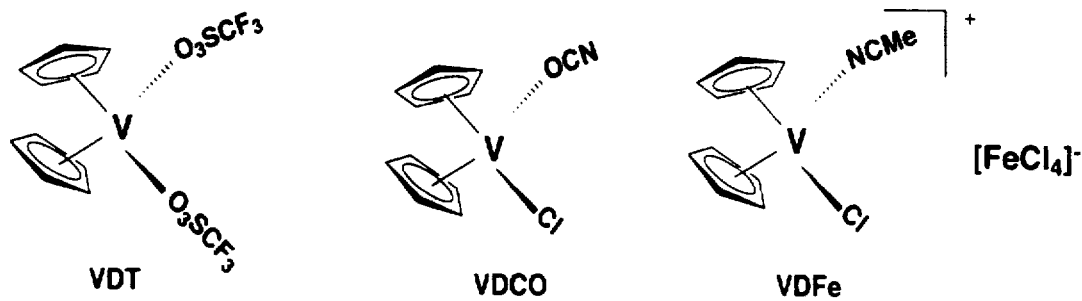
FIG. 1

FIG. II A
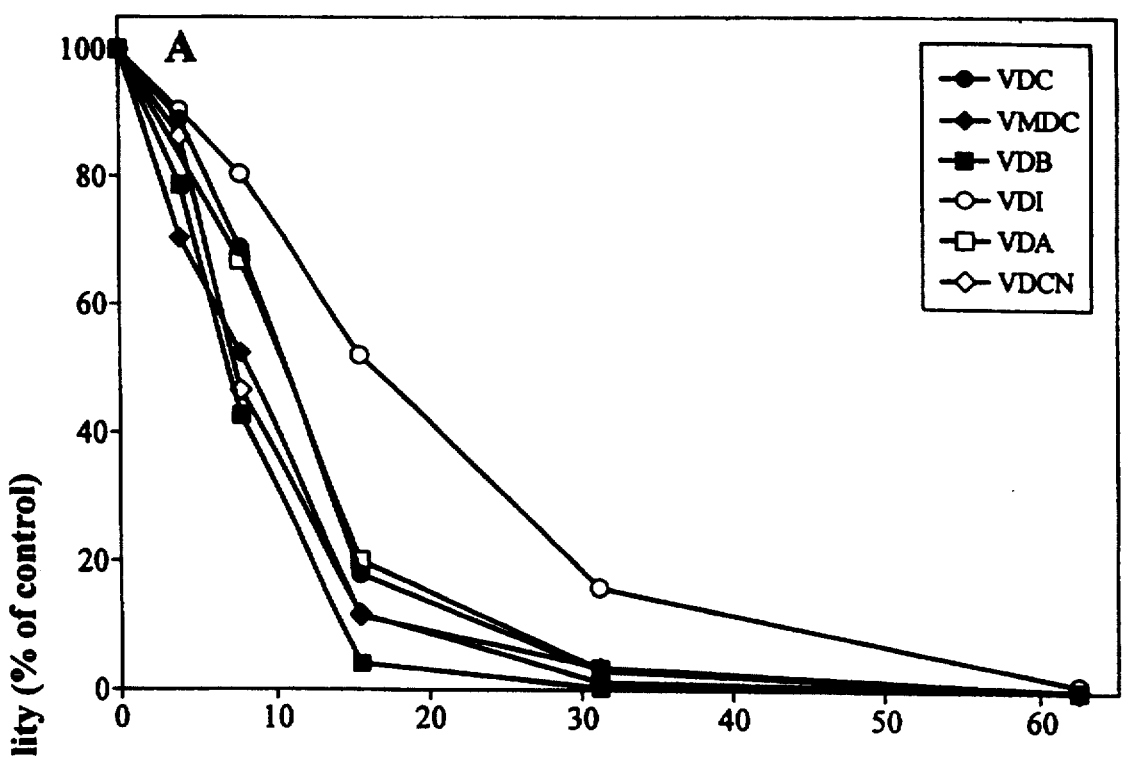
FIG. II B
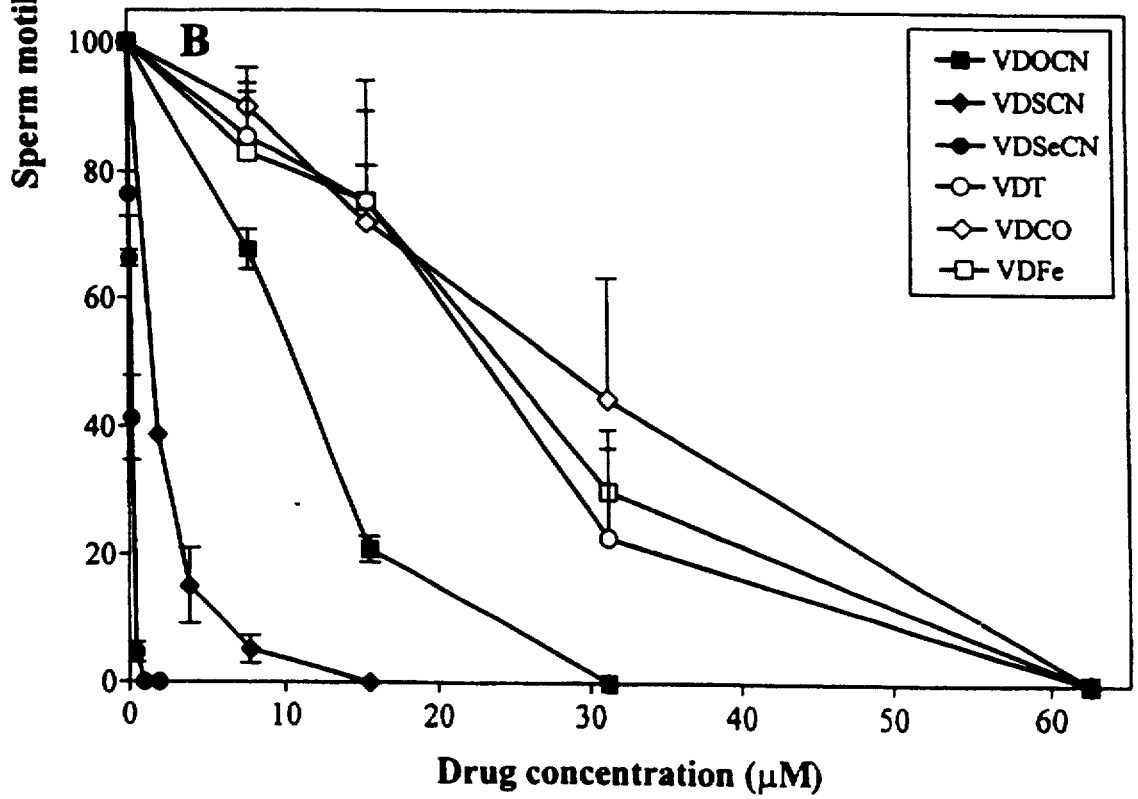

VANADIUM (IV) METALLOCENE COMPLEXES HAVING SPERM MOTILITY INHIBITING ACTIVITY

FIELD OF THE INVENTION

This invention relates to metallocene compositions containing vanadium (IV). More particularly, the invention relates to Vanadium (IV) complexed metallocene, having spermicidal activity.

BACKGROUND OF THE INVENTION

The known spermicidal agents, nonoxynol-9 and gramicidin, exert their effects via a detergent-like ability to damage the sperm plasma membrane, perturb its conformation and destroy its semi-permeable nature thereby impairing the sperm motility and egg fertilizing functions (Wilborn, et al., *Fertil Steril* 1983; 39:717–719; Bourinbaiar, et al., *Life Sci* 1994; 54:PL 5–9). Because of their nonspecific membrane disruptive properties, such vaginal spermicides have been shown to damage the cervicovaginal epithelium, as well, which may lead to a lower degree of protection from sexually transmitted diseases (Niruthisard, et al., *Sex Transm Dis* 1991; 18:176–179). A novel vaginal contraceptive preferably does not function with the non-specific membrane toxicity mediated by detergent-type action of the currently available vaginal contraceptives.

Vanadium is a physiologically essential element which can be found in one of five (I to V) oxidation states. Several inorganic salts containing vanadium with oxidation state +4 (IV) have been shown to function as modulators of cellular redox potential and to exert pleiotropic effects in multiple biological systems by catalyzing the generation of reactive oxygen intermediates. See, for example, Shi, et al., *Ann Clin Lab Sci* 1996; 26:390–49; Byczkowski, et al., *Bull Environ Contam Toxicol* 1988; 41:696–703; Younes, et al., *Toxicology* 1991; 66:63–74, and Sakurai, et al., *Biochem Biophys Res Commun* 1995; 206:133–137. Reactive oxygen intermediates have been reported to affect sperm motility by a combination of peroxidation of membrane lipids and proteins (Aitken, et al., *Biol Reprod* 1989; 40:183–197; Jones, et al., *Fertil Steril* 1979; 31:531–537). Peroxidative damage to the sperm plasma membrane is an important pathophysiological mechanism in the onset of male infertility (Aitken, et al., *BioEssays* 1994; 16:259–267). It has also been shown that superoxide radicals generated by the action of xanthine oxidase exert a direct, suppressive effect on many aspects of sperm function (Aitken, et al., *J. Reprod. Fertil.* 1993; 97:441–450). Sperm are thought to be particularly susceptible to oxidative stress by virtue of their high content of unsaturated fatty acids and their relative paucity of cytoplasmic enzymes for scavenging the reactive oxygen intermediates that initiate lipid peroxidation (Alvarez, et al., *J. Androl* 1987; 8:338–348).

There is a need for new spermicidal compounds for contraceptive purposes. The ability of vanadium IV containing organometallic complexes to catalyze the generation of reactive oxygen species was evaluated for its potential to impact sperm activity. Results of studies with structurally distinct organometallic complexes containing vanadium (IV) surprisingly demonstrated these compounds to be potent spermicidal agents at nano-micromolar concentrations. These compounds have also surprisingly been found to exhibit selective apoptosis-inducing activity against testicular germ cells in vivo.

SUMMARY OF THE INVENTION

Organometallic complexes containing vanadium (IV), including vanadocene dichloride (VDC), bis (methylcyclopentadienyl) vanadium dichloride (VMDC), vanadocene dibromide (VDB), vanadocene diiodide (VDI), vanadocene diazide (VDA), vanadocene dicyanide (VDCN), vanadocene dioxycyanate (VDOCN), vanadocene dithiocyanate (VDSCN), vanadocene diselenocyanate (VDSeCN), vanadocene ditriflate (VDT), vanadocene monochloro oxycyanate (VDCO), and vanadocene monochloro acetonitrilo tetrachloro ferrate (VDFE) were found to have spermicidal activity. Specifically, the "vanadocene" complexes elicited potent spermicidal activity at nano-micromolar concentrations with an order of efficacy VDSeCN>VDSCN>VDB>VMDC>VDA>VDC>VDI>VDT>VDFE>VDCO. In contrast, control metallocene complexes containing titanium, zirconium, molybdenum, and hafnium lacked spermicidal activity.

Accordingly, the present invention includes a contraceptive composition containing a spermicidal effective amount of an organometallic cyclopentadienyl vanadium IV complex and a pharmaceutically acceptable carrier, diluent or vehicle.

Another aspect of the present invention is a method of contraception including the step of contacting sperm with a spermicidal effective amount of an organometallic cyclopentadienyl vanadium IV complex.

Yet another embodiment of the invention utilizes the selective apoptotic-inducing properties of organometallic cyclopentadienyl vanadium IV complexes against testicular germ cells to selectively kill normal testicular germ cells and testicular germ cell tumors.

BRIEF DESCRIPTION OF THE DRAWINGS

FIGS. 11A and 11B are graphs showing dose response curves for twelve vanadocene complexes on sperm motility, including VDC, VMDC, VDB, VDI, VDA, and VDCN in FIG. 11A, and VDO, VDSCN, VDSeCN, VDT, VDCO, and VDFe in FIG. 11B.

DETAILED DESCRIPTION

Figure 1A:
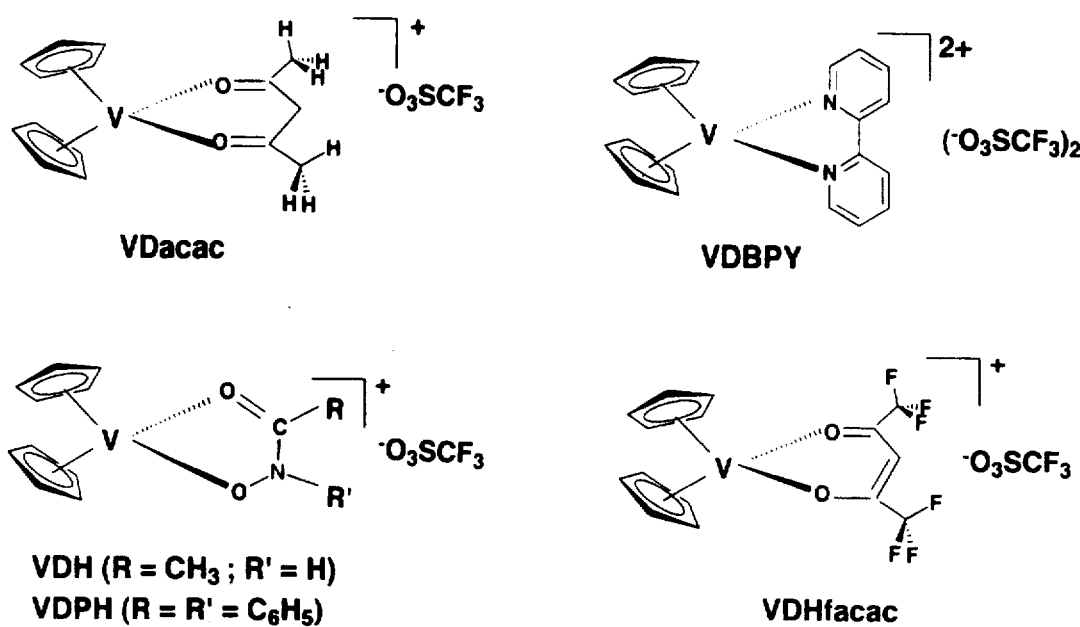
FIG. 1 shows chemical structures for the various metallocene complexes.

The present invention concerns metallocenes. These are so-called "bent-sandwich" metallocene complexes where cyclopentadienyl moieties in a tetrahedral symmetry are positioned in a bent conformation with respect to the metal center. Structures of typical metallocenes are shown in FIG. 1.

The present invention concerns the finding that certain metallocenes have potent and selective spermicidal activity. These are particularly the cyclopentadienyl metallic complexes where the metal is vanadium having an oxidation state of +4 (IV). Thus, as potent spermicide compounds, these cyclopentadienyl vanadium +4 complexes may be formulated by known methods into pharmaceutical compositions for selective killing of sperm cells, e.g., for contraceptive use and/or selective killing of testicular germ cells in vivo.

The following glossary of metallocenes is provided to clarify terms used throughout the specification:

Group A: Metallocene Dichlorides
VDC Vanadocene dichloride ($Cp_2VCl_2$)
TDC Titanocene dichloride ($Cp_2TiCl_2$)
ZDC Zirconocene dichloride ($Cp_2ZrCl_2$)
MDC Molybdocene dichloride ($Cp_2MoCl_2$)
HDC Hafnocene dichloride ($Cp_2HfCl_2$)
Group B: Vanadocene Dihalides
VDC Vanadocene dichloride ($Cp_2VCl_2$)
VMDC Bis (methyl cyclo pentadienyl) vanadium dichloride [$(MeCp)_2VCl_2$)]
VDB Vanadocene dibromide ($Cp_2VBr_2$)
VDI Vanadocene diiodide ($Cp_2VI_2$)
Group C: Vanadocene Di-Pseudohalides
VDA Vanadocene diazide [$Cp_2V(N_3)_2$]
VDCN Vanadocene dicyanide ($Cp_2V(CN)_2$)
VDOCN Vanadocene dioxycyanate ($Cp_2V(OCN)_2$)
VDSCN Vanadocene dithiocyanate ($Cp_2V(SCN)_2$)
VDSeCN Vanadocene diselenocyanate ($VCp_2(SeCN)_2$)
Group D: Vanadocene Disubstituted Derivatives
VDT Vanadocene ditriflate ($Cp_2V(O_3SCF_3)_2$)
VDCO Vanadocene monochloro oxycyanate ($Cp_2V(OCN)(Cl)$)
VDFe Vanadocene monoacetonitrilo monochloro tetrachloro ferrate ($Cp_2VClNCCH_3$) $FeCl_4$
Group E: Chelated Vanadocene Complexes
VDacac Vanadocene acetylacetonato monotriflate ($Cp_2V(CH_3COCH_2COCH_3)(O_3SCF_3)$)
VDBPY Vanadocene bipyridino ditriflate ($Cp_2V(C_{10}H_8N_2)(O_3SCF_3)_2$)
VDHfacac Vanadocene hexafluoro acetylacetonato monotriflate ($Cp_2V(CF_3COCH_2COCF_3)(O_3SCF_3)$)
VDH Vanadocene acethydroxamato monotriflate ($Cp_2V(CH_3CON(O)H)(O_3SCF_3)$)
VDPH Vanadocene N-phenyl benzohydroxamato monotriflate ($Cp_2V(C_6H_5CON(O)C_6H_5)(O_3SCF_3)$)

The spermicidal compositions of the present invention are suitable for use in mammals. As used herein, the term "mammals" means any class of higher vertebrates that nourish their young with milk secreted by mammary glands, e.g., humans, rabbits and monkeys.

The spermicides useful in accordance with the present invention are the above-mentioned vanadocenes where the vanadium metal has an oxidation state of +4, and include those described above.

Thus, the contraceptive compositions of the present invention contain one of the above-mentioned vanadocene complexes. The total amount of spermicide thereof will typically range from about 0.05 to 0.5 weight percent based on the weight of the contraceptive composition. Preferably, the amount of spermicide employed will be that amount necessary to achieve the desired spermicidal results. Appropriate amounts can be determined by those skilled in the art. Preferably, the amount of the spermicide employed, a spermicidal effective amount, will comprise from about 0.0025 to 0.025 weight percent, and more preferably from about 0.05 to 0.5 weight percent, based on the weight of the contraceptive composition.

When used in vivo to selectively kill testicular germ cells or testicular germ cell tumors, the administered dose is that effective to have the desired effect, e.g., sufficient to kill essentially all normal germ cells for chemical castration, or sufficient to reduce or eliminate a testicular cell tumor. The appropriate dose can be extrapolated using known methods and relationships. A useful dose will vary with the desired effect, the mode of administration, and the composition administered. In general, the desired dose will be in the range of 1–25 mg/kg body weight.

The compositions of the invention contain not only the spermicide but necessarily pharmaceutically acceptable carriers, diluents or vehicles, i.e., one that appropriately delivers vanadocene complexes to a site for contact with sperm or germ cells and provides spermicidal and/or anti-germ cell activity.

One advantageous component in the pharmaceutical composition for administration of a spermicide is a polymeric delivery component as described in U.S. Pat. No. 5,595,980, which patent is incorporated herein by reference. It has been found that such polymeric delivery component enhances effectiveness of a spermicide and reduces vaginal irritation on administration.

In addition to the polymeric component, the balance of the contraceptive compositions, i.e., typically from about 0.1 to 99.8% and often about 50 to 99.8 weight percent, may optionally comprise one or more cosmetic ingredients. Such cosmetic ingredients are known to those skilled in the art and are often referred to in the art as diluents, solvents and adjuvants. Typically cosmetic ingredients include, for example; water, ethyl alcohol, isopropyl alcohol, glycerin, glycerol propylene glycol, sorbitol and other high molecular weight alcohols. In addition, contraceptive compositions may contain minor amounts, e.g. from about 0.1 to 5% weight based on the weight of the contraceptive compositions, of other additives, such as, for example; stabilizers, surfactants, menthol, eucalyptus oil, other essential oils, fragrances, and the like. Polyoxyethylene 20 sorbitan monolaurate is a preferred stabilizer for use in the compositions. Details concerning the selection and amounts of cosmetic ingredients, other additives, and blending procedures are known to those skilled in the art.

The contraceptive compositions of the present invention may be delivered to the vagina of a mammal by any means known to those skilled in the art. Typical forms for delivery of the compositions include, for example; creams, lotions, gels, foams, sponges, suppositories and films. In addition, the compositions of the present invention may be used as personal care lubricants, such as, for example, condom lubricants, and the like. Such lubricants may comprise commonly known ingredients such as, for example: humectants; e.g., glycerin, sorbitol, mannitol, glycols and glycol ethers; buffers, e.g., glucono-d-lactone; germicides or bactericides; e.g., chlorhexidine gluconate; preservatives, e.g., methylparaben; viscosifiers; e.g., hydroxyethyl cellulose, etc.; other adjuvants; e.g., colors and fragrances; in addition to the compositions of the present invention. Those skilled in the art will recognize that the physical properties, e.g., viscosity, of such delivery forms may vary widely. For example, the viscosity of a gel form of the composition of the present invention, e.g., 150,000 centipoise, may be substantially higher than the viscosity of lotion form of the composition of the present invention, e.g., 100 centipoise. Further details concerning the materials, ingredients, proportions and procedures of such delivery forms are known to those skilled in the art.

The contraceptive compositions of the present invention are preferably administered to the vagina of the mammal in a dosage which is effective to immobilize sperm present in the vagina and/or to inhibit their penetration in cervical mucus. Typical dosages range between about 0.0001 to 0.001 grams of the composition per kilogram of body weight of the mammal.

Inter-vaginal devices may also be used to aid in the administration of the spermicide as described in U.S. Pat. No. 5,069,906.

In administering the spermicide in the form of the above compositions, the compositions may also be formulated to release the spermicide both rapidly and with a prolonged release of the drug. Such a formulation providing both rapid and prolonged release has been described in U.S. Pat. No. 4,707,362, which patent is also incorporated herein.

In administering the spermicide in vivo, it is understood that multiple delivery methods are available, including injection, both systemic and local. The preferred method of delivery is local, e.g., intratesticular injection. Where appropriate, the composition may be directly injected into a testicular germ cell tumor mass.

The invention may be further clarified by reference to the following Examples, which serve to exemplify some of the preferred embodiments, and not to limit the invention.

EXAMPLES

Example I

Effect of Metallocenes-Containing Vanadium (IV) on Sperm Function

A. Synthesis of Metallocene Complexes Containing Vanadium (IV) or Other Metals

The chemical compositions of the various organometallic cyclopentadienyl metal (metallocene) complexes analyzed in this study are depicted in FIG. 1. The metallocene [Bis(cyclopentadienyl) metal (M) (IV)] dichloride complexes, vanadocene dichloride ($Cp_2VCl_2$=VDC), titanocene dichloride ($CP_2TiCl_2$=TDC), zirconocene dichloride ($CP_2ZrCl_2$=ZDC), and molybdocene dichloride ($CP_2MoCl_2$=MDC) were synthesized according to the published procedures of Wilkinson, et al., *J Am Chem Soc* 1954; 76:4281–4284 and G. Wilkinson, *Comprehensive Organometallic Chemistry, Pergamon* 1982, 3:554–646. Hafnocene dichloride ($CP_2HfCl_2$=HDC) was purchased from Aldrich Chemical Co. Milwaukee, WI. Vanadocene dihalides [$CP_2VBr_2$=VDB; $(MeCp)_2VCl_2$=VMDC] and vanadocene di-pseudohalides [$CP_2V(N_3)_2$=VDA; $CP_2V(CN)_2$=VDCN; $CP_2V(NCO)_2$=VDOCN; $Cp_2V(NCS)_2$=VDSCN] were synthesized according to the published procedures of Petersen, et al., *J Am Chem Soc* 1975; 97:6422–6433 and Doyle, et al., *Inorg. Chem.* 1968; 7:2479–2484. Two novel derivatives of vanadocene halides, $Cp_2VI_2$=VDI (halide) and $Cp_2V(NCSe)_2$=VDSeCN (pseudohalide), and three vanadocene disubstituted derivatives, [$Cp_2V(O_3SCF_3)_2$=VDT; $Cp_2VCl(CH_3CN)$ $(FeCl_4)$=VDFe; and $Cp_2V(OCN)$ $(Cl)$=VDCO] were synthesized for this study according to the method described in Dorer et al., 1997, *Collect. Czech. Chem. Comm* 62:265–277, and Thewalt et al., 1995, *Transition Metal Chem* 10:393–395. For each compound, purity was >99%, as determined by the $^1H$ NMR (Varian 300 MHz), infra red (FT-Nicolet model Protege 460) spectroscopy, UV-Vis (DE 7400 spectrophotometer) spectroscopy and elemental analysis. Cisplatin (cis-) diamino-dichloroplatinum(II) [CDDP], sodium orthovanadate and sodium metavanadate were purchased from Sigma Chemical Co., St. Louis, MO.

Five chelate complexes of vanadocene derivatives were also synthesized for this study. These complexes included VDacac, VDBPY, VDHfacac, VDH, and VDPH. Two of these chelate complexes, VDacac and VDHfacac, were synthesized according to the procedures of Doyle, et al., 1968, *Inorg. Chem.* 7:2479–2484. Three other new chelated vanadocene complexes, VDH, VDPH, and BDBPY were synthesized.

B. Isolation of Motile Fraction of Sperm

All studies involving human subjects were approved by the Institutional Review Board of The Wayne Hughes Institute. Semen was provided by 12 healthy volunteers who had been repeatedly found to have normospermic semen according to World Health Organization criteria for normal donor specimen. Semen samples were allowed to liquefy for 30 minutes at 37° C. after which an aliquot was removed for analysis of motion in a computer assisted sperm analyzer (CASA). The remainder of the sperm was diluted 1:1 with modified Biggers, Whitten, and Whittingam's medium (BWW, Biggers, et al., In: Daniel J. C. Jr. (ed.), "Methods in Mammalian Embryology", San Francisco: Freeman; 1971:86–116) containing 25 mM HEPES (Irvine Scientific Co., Santa Ana, CA), layered on discontinuous (90–45%) Percoll gradients (Conception Technologies, San Diego, CA) and centrifuged at 400×g for 20 minutes at room temperature (RT). The sperm pellets were washed twice by centrifugation (500×g for 5 minutes) with 5 ml each of BWW medium supplemented with 0.3% (w/v) BSA (Fraction V, Sigma Chemical Co.; [BWW-0.3% BSA]), resuspended in 1.5 ml aliquots in BWW-3% BSA and centrifuged (500×g for 4 minutes). The tubes were incubated at a 45° angle for 3 hours at 37° C. in a 5% $CO_2$ atmosphere. Following this interval of "swim-up" and exposure to capacitating conditions, the supernatant containing >95% motile sperm was pelleted and resuspended in BWW-0.3% BSA to a concentration of $50\times10^6$/ml.

In experiments comparing the effects of the metallocene dichlorides (VDC, TDC, ZDC, MDC, and HDC), vanadocene halides (VDB, VDC, VMDC, and VDI), and vanadocene dipseudohalides (VDA, VDCN, VDOCN, VDSCN, and VDSeCN), and vanadocene disubstituted derivatives (VDT, VDCO, and VDFe) on human sperm motility, the stock solutions (100 mM) of the compounds were freshly prepared in dimethylsulfoxide (DMSO) and further diluted in 2 ml of BWW-0.3% BSA medium to yield 250 µM. Serial two-fold dilutions were made in BWW-0.3% BSA medium to yield concentration ranges from 250 µM to 1.9 µM. Control tubes consisting of BWW-0.3% BSA medium containing 0.25% of DMSO alone were used for solvent control.

C. Sperm Immobilization Assay (SIA)

To evaluate the spermicidal activity of the metallocene complexes, highly motile fractions of sperm ($>10 \times 10^6$), prepared from pooled donor sperm specimens (n=5) were incubated in 1 ml of BWW-0.3% BSA (pH 7.4), containing serial two-fold dilutions of the test compound (250 µM to 1.9 µM). After 3 hours of incubation at 37° C., 4 µl aliquots of sperm were transferred to two 20 µm Microcell chambers (Conception Technologies), and sperm motility was assessed by CASA. Sperm motility in sham-treated control suspensions of motile sperm (i.e., similarly processed sperm suspended in 1 ml of the corresponding medium containing 0.25% DMSO in the absence of metallocene complexes) was determined for comparison. Sperm immobilizing assays evaluating the time kinetics and dose dependency of the spermicidal effects of the metallocene complexes were performed in BWW medium-0.3% BSA.

In experiments designed to determine the effects of the vanadocene dihalide on sperm acrosome reaction, motile fractions of sperm ($15 \times 10^6$/ml) prepared from 3 normal donors were incubated in 1 ml of BWW-0.3% BSA in the presence of 100 µM VDC in 0.1% DMSO or DMSO (0.1%) alone at 37° C. At 0, 3, 6, 12 and 24 hour time points, sperm suspensions were washed in BWW without protein, fixed, and permeabilized with 95% ethanol, and the air-dried sperm smears were stained with fluorescein (FITC)-conjugated Pisum sativum lectin (Sigma Chemical Co.). The percentages of sperm with an intact acrosome were determined by evaluating 200 sperm using fluorescence microscopy (Olympus BX-60 microscope, Lake Success, NY). In positive control samples, the acrosomal loss was induced by incubating the sperm suspension with the nonoxynol9 (IGEPAL CO-630; Rhone-Poulenc, Cranbury, NJ) at a final concentration of 100 µM in assay medium for 3 hours at 37° C.

In experiments designed to examine the kinetics of sperm immobilization by vanadocene complexes, 1 ml aliquots of highly motile fraction of sperm ($15 \times 10^6$) or a 1:1 dilutions of liquified semen in BWW medium were mixed with 2 µl of freshly prepared stock (100 mM) solutions of 4 vanadocene dihalides (VDB, VDC, VMDC, and VDI) and 5 vanadocene di-pseudohalides (VDA, VDCN, VDOCN, VDSCN, and VDSeCN) and 3 vanadocene disubstituted derivatives (VDT, VDCO and VDFe) to yield a final concentration of 200 µM. A corresponding volume of DMSO (0.2%) was added to control tubes. Following addition of the test compounds, 4 µl aliquots were immediately transferred to pre-warmed 20 µm Microcell chambers and the time (in seconds) required to completely immobilize sperm was recorded using CASA.

In experiments designed to assess reversibility of sperm immobilization after removal of VDC, liquefied semen was divided into two aliquots. One aliquot was diluted four-fold in phosphate-buffered saline (PBS) and used for CASA. The other aliquot was used to isolate motile fraction of sperm by two-layer percoll gradient fractionation and resuspension in assay medium. Aliquots (0.5 ml) of semen ($40 \times 10^6$ sperm/ml) or motile sperm fraction ($20 \times 10^6$/ml) in BWW-0.3% BSA medium were mixed with 0.5 µl of freshly prepared stock (100 mM) solution of VDC to yield 100 µM. Corresponding volume (0.1%) of DMSO was added to control tubes containing assay medium. After 15 and 30 seconds of addition, the suspension was rapidly diluted in BWW-0.3% BSA medium and centrifuged (500×g for 5 min). The supernatants from washed samples were discarded, and the pellets were resuspended in 0.5 ml each of BWW-0.3% BSA medium (without VDC or DMSO). Following a 15 minute incubation at 37° C., duplicate aliquots were reassessed for sperm motion parameters by CASA. The results were compared to the sperm motion parameters of similarly processed sperm suspensions of motile sperm suspended in medium lacking VDC.

In experiments designed to evaluate the effects of the pH of the assay medium on sperm motility in the presence and absence of VDC (100 µM), the assay medium (BWW-0.3% BSA) was adjusted to pH 6.0, 6.5, 7.0, 7.5, 8.0, or 8.5. Percoll-gradient fractionated, swim-up sperm ($8 \times 10^6$/ml) obtained from pooled donor sperm specimens (n=4) were washed in BWW-0.3% BSA medium of appropriate pH prior to their addition to the reaction mixture. After 3 hours incubation at 37° C., sperm motility was assessed by CASA, as described below.

D. Sperm Kinematic Parameters

Sperm motility parameters were determined, as described in L. J. Burkman, Fertil Steril 1991; 55:363–371. Four µl of each sperm suspension ($>10 \times 10^6$/ml) was loaded into two 20 µm Microcell chambers that were placed onto a counting chamber at 37° C. At least 8–10 fields per chamber were scanned for analysis using a Hamilton Thorne integrated visual optical system (IVOS), version 10 machine (Hamilton Thorne Research Inc., Danvers, MA), run at 37° C. Each field was recorded for 30 seconds. The Hamilton Thorne computer calibrations were set at 30 frames at a frame rate of 30/s; microscope stage temperature was maintained at 37° C. with stage warmer; minimum contrast 8; minimum size 6; low-size gate, 1.0; high-size gate, 2.9; low-intensity gate, 0.6; high-intensity gate, 1.4; phase-contrast illumination; low path velocity at 10 µm/s, and threshold straightness at 80%; HTM magnification factor, 1.95. The performance of the analyzer was periodically checked using the play-back function.

The kinematic parameters determined for each sperm sample included numbers of motile (MOT) and progressively (PRG) motile sperm; curvilinear velocity (VCL; a measure of the total distance traveled by a given sperm during the acquisition divided by the time elapsed); average path velocity (VAP; the spatially averaged path that eliminates the wobble of the sperm head), straight line velocity (VSL; the straight-line distance from beginning to end of track divided by time taken), beat cross frequency (BCF, frequency of sperm head crossing sperm average path), the amplitude of lateral head displacement (ALH; the mean width of sperm head oscillation) and the derivatives, straightness (STR=100×VAP/VCL); linearity (LIN=100× VSL/VCL; departure of sperm track from a straight line). Data from each individual cell track were recorded and analyzed. At least 200 sperm were analyzed for each aliquot sampled.

E. Confocal Laser Scanning Microscopy

Confocal microscopy was performed using BioRad MRC-1024 Laser Scanning Confocal Microscope (BioRad, Hercules, CA) equipped with an argon-ion laser (excitation lines at 488, 568, and 647 nm) and mounted on a Nikon Eclipse E800 series upright microscope equipped with high numerical aperture objectives. For confocal images, three fluorescent markers, FITC-Pisum sativum (Sigma Chemical Co.), TOTO-3 (Molecular Probes, Eugene, OR) and Nile red (Molecular Probes) were selected because their targets are different (acrosome, nucleus, and plasma membrane of permeabilized sperm, respectively). Stock solutions (1 mg/ml) of TOTO-3 and Nile red were made in DMSO and used at dilution of 1:1000. Ethanol permeabilized and air-dried sperm smears were stained sequentially with the three fluorescent markers. Using fluorescence imaging cytometry, the fluorescence emission of fluorescein, TOTO-3, and Nile red, accumulated in the acrosomal region, nucleus, and the plasma membrane of sperm after ethanol permeabilization, was simultaneously recorded. Nile Red, FITC, and TOTO-3 fluorescence were simultaneously detected using the 598/40 nm, 522 DF32, and 680 DF32 emission/filter, respectively. Confocal images were obtained using a Nikon 60 x NA 1.4) objective and Kalman collection filter. Digitized fluorescent images were saved on a Jaz disk and processed with the Adobe Photoshop software (Adobe Systems, Mountain View, CA). Final images were printed using a Fujix Pictography 3000 (Fuji Photo Film Co., Tokyo, Japan) color printer.

F. Low Voltage Scanning Electron Microscopy

High-resolution low-voltage scanning electron microscopy (HR-LVSEM) was utilized for topographical imaging of different membrane domains over the sperm head, as described in Stoffel, et al., *Molecular Reprod Develop* 1993; 34:175–182. This approach provides information on the true surface due to decreased sample penetration by the electron beam, Erlandsen, et al., *Scanning* 1989; 11:169–175. Aliquots ($20 \times 10^6$/ml) of highly motile suspensions of sperm were incubated with 0.1% DMSO alone or 100 µM of VDC in 0.1% DMSO or 10 µM CaI in 0.1% DMSO for 3 hours at 37° C. For HR-LVSEM, washed suspensions of sperm were placed on 0.1% poly-L-lysine-coated glass chips and allowed to adhere to the glass over a 1 hour incubation period at 4° C. The supernatants were decanted, and adherent cells were fixed in 1% paraformaldehyde and 1% glutaraldehyde in 0.14 M sodium cacodylate buffer for 3 hours. In order to preserve the plasma membrane integrity, sperm were post-fixed in 1% osmium tetroxide ($OsO_4$) containing 0.1% ruthenium red in 0.14 M cacodylate buffer for 1 hour at 4° C. All samples were dehydrated through an ascending ethanol series, critical point dried, and coated with approximately 2 nm of platinum using ion beam sputtering with argon (4 mA at 10 ke V; Ion Tech Ltd., Middlesex, England). All samples were examined using a Hitachi S-900 SEM at an accelerating voltage of 2 keV. Sperm were observed under low power magnification ($\times 2,000$–5000) and representative sperm were photographed under intermediate magnification ($\times 18,000$–25,000). In each specimen evaluated, at least 200 sperm were scanned for the intactness of the acrosomal region.

G. Statistical Analysis

Results for the various numerical sperm function parameters are presented as mean±SD values. Comparisons between VDC-treated sperm relative to sperm motility parameters and acrosomal loss were performed using a paired, two-tailed Student's t-test. A p value of <0.05 was considered significant. Non-linear regression analysis was used to find the $EC_{50}$ values (i.e., concentrations of compound that result in 50% sperm motility loss) from the concentration effect curves using GraphPad software (San Diego, CA).

RESULTS

H. Spermicidal Activity of Vanadocene Dichloride (VDC)

Figure 2:
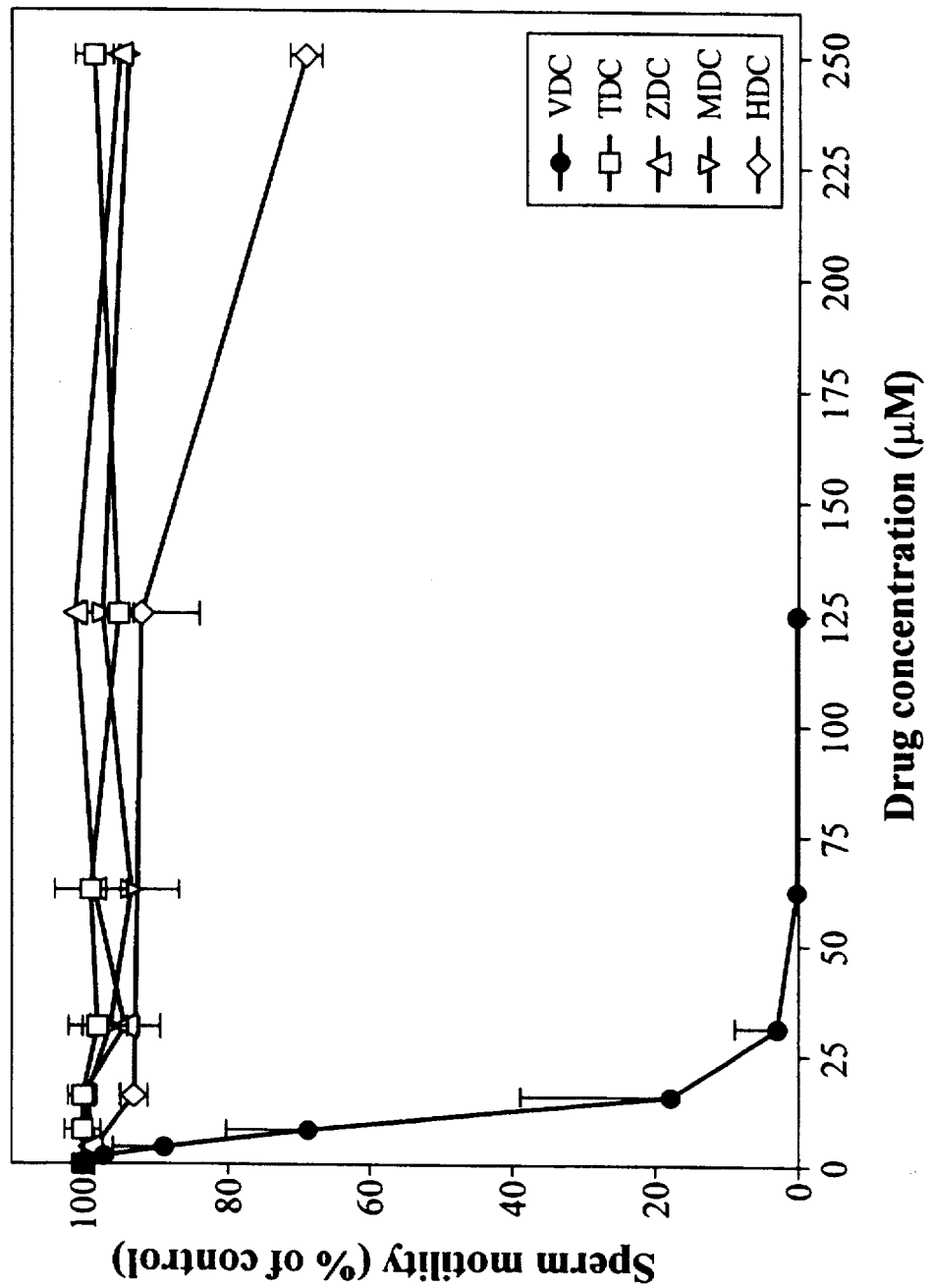
FIG. 2 shows dose-response curves for 5 metallocene dichlorides on human sperm motility.

A highly motile fraction of sperm was incubated for 3 hours with increasing two-fold concentrations of metallocene dichlorides, VDC, TDC, ZDC, MDC, and HDC (1.9 µM–250 µM) or 0.25% DMSO alone in the assay medium, and the percentage of motile sperm were evaluated using a computer-assisted sperm motion analyzer as described above for Example IB. The effects of a 3 hour incubation in BWW-0.3% BSA medium with the metallocene dichlorides, VDC, TDC, ZDC, MDC, and HDC on human sperm motility at 8 different concentrations ranging from 1.9 µM to 250 µM were examined. Each data point represents the mean±SD values from three to five independent experiments. As shown in FIG. 2, exposure of highly motile sperm to the vanadium (IV) containing VDC resulted in a dose-dependent inhibition of sperm motility with an $EC_{50}$ value of 9.6 µM (95% CI: 6.9–15.3 µM; mean of 5 experiments). At concentrations >25 µM, VDC abrogated the motility of >95% of the treated sperm. Surprisingly, other metallocene dichlorides containing titanium (TDC), zirconium (ZDC), or molybdenum (MDC), as central metal atoms (oxidation state IV) had no effect on sperm motility, even at 250 µM, and hafnodium-containing HDC showed only a 31% reduction in sperm motility at 250 µM. These results demonstrated that VDC is an effective inhibitor of human sperm motility and this spermicidal activity is dependent on the central metal atom vanadium (IV) within the cyclopentadienyl metal complex.

Motile fractions of sperm were incubated in assay medium in the presence of 5 increasing concentrations of VDC (0, 3.9, 7.8, 15.6, 31.2, and 62.5 µM) in 0.25% DMSO or DMSO alone for 3 hours at 37° C., and the motility characteristics were determined using the Hamilton Thome-IVOS version 10 computer assisted sperm analyzer.

Figure 3:
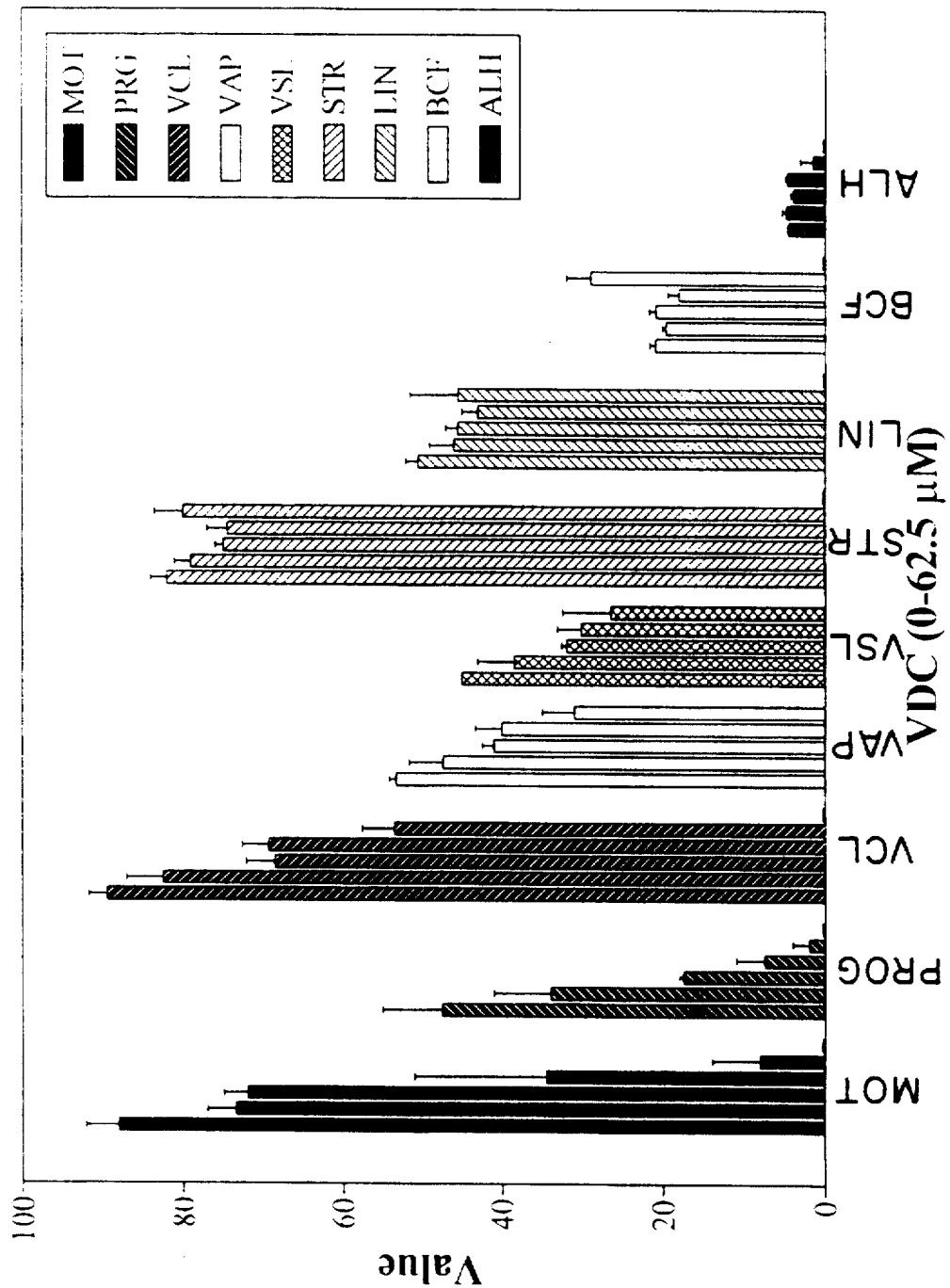
FIG. 3 shows effects of vanadocene dichloride on sperm motion parameters.

The observed decrease in sperm motility (% motility, MOT; % progressive motility, PRG) after exposure to VDC was associated with significant changes (p<0.05) in the movement characteristics of the surviving sperm, particularly with respect to the track speed (VCL), path velocity (VAP), and straight line velocity (VSL) [FIG. 3]. The decreases in VCL and VAP were similar in magnitude. Therefore, the straightness (STR) of the swimming pattern was not altered at lower concentrations (3.9 to 31.2 µM) of VDC. Similarly, the decreases in VCL and VSL were similar in magnitude. Therefore, the linearity (LIN) of the sperm tracks was not altered either. Also, the beat-cross frequency (BCF), and the amplitude of lateral sperm-head displacement (ALH) were relatively uniform as the proportion of motile sperm declined with increasing concentration (3.9, 7.8, 15.6, 31.2 and 62.5 µM) of VDC. The sperm motion parameters of control sperm did not show any significant changes during the 3 hour observation period.

Example II

Apoptosis Mediated by Metallocenes Containing Vanadium (IV)

A. Analysis of Vanadocene Metallocomplex-Mediated Apoptosis by FITC Annexin V Binding Assay In order to explore if the irreversible nature of the spermicidal activity of VDC could be due to induction of apoptosis following the loss of sperm motility, the surface binding of FITC-labeled recombinant human Annexin V to VDC-treated sperm as a function of time was examined using flow cytometry. The sperm in the swim-up fractions were identified by the characteristic forward and 90° angle light scatter (D'Cruz, et al., *Biol Reprod* 1995; 53:1118–1130). One ml aliquots of highly motile sperm ($5 \times 10^6$) were incubated in the absence and presence of 100 µM of VDC in 0.1% DMSO or 8 mM of hydrogen peroxide ($H_2O_2$), as described above. At intervals of 0, 1, 2, 4, 8 and 12 hours, sperm were washed with Tyrode's salt solution (Sigma Chemical Co.) supplemented with 1% BSA (1% TBSA), and the pellets were resuspended in the same medium. The sperm suspension was reacted for 30 minutes in the dark at RT with saturating (6 µg/ml in 1% TBSA) concentration of FITC-conjugated recombinant human Annexin V (Caltag Laboratories, San Francisco, CA). After two washes in Tyrode's salt solution, sperm were resuspended in 1% TBSA containing 10 μg/ml propidium iodide (PI; Molecular Probes) and analyzed by FACS. Annexin V and PI binding were simultaneously measured in VDC-exposed and control sperm. All analyses were done at 488-nm excitation from an argon laser. FITC-Annexin V and PI emissions were split with a 600-nm short-pass dichroic mirror; and 575-nm band pass filter was placed in front of one photomultiplier tube to measure FITC emission, and a 635-nm band pass filter was used for PI emission (Vermes, et al., *J Immunol Meth* 1995; 184:39–51). The percentage of sperm positive for Annexin V and PI were determined using the cutoff signals for membrane-intact motile sperm. The M1 and M2 gates were used to demarcate non-apoptotic and apoptotic sperm populations respectively. Three separate experiments were performed to assess the surface expression of phosphatidyl serine following exposure of sperm to VDC and $H_2O_2$.

In studies to evaluate the comparative effect of 4 vanadocene dihalides (VDB, VDC, VMDC, and VDI) and 5 vanadocene di-pseudohalides (VDA, VDCN, VDOCN, VDSCN, and VDSeCN) and 3 vanadocene disubstituted derivatives (VDT, VDCO, and VDFe) to induce apoptosis, 1 ml aliquots of motile sperm ($10^7$/ml) in duplicate were incubated in BWW-0.3% BSA at 37° C. for 12 hours with and without 100 μM each of the test compounds. Sperm incubated with 8 mM $H_2O_2$ served as a positive control. The percentage of Annexin V-positive sperm were quantitated by the flow cytometric FITC-Annexin V binding assay, as described above.

RESULTS
B. Apoptosis Shown by Annexin V Binding

Figure 8:
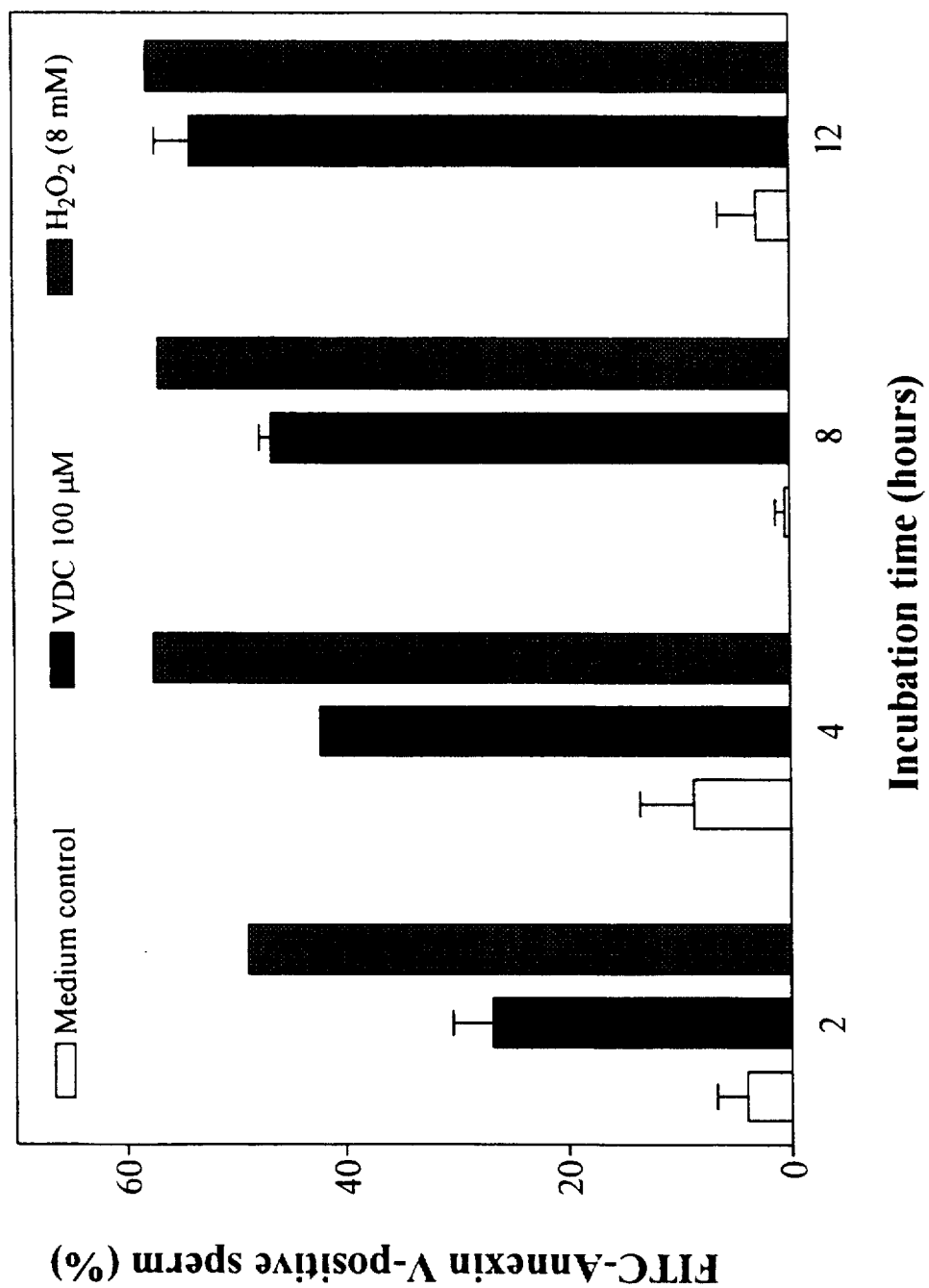
FIG. 8 is a bar graph illustrating time-course of apoptosis induced by VDC measured by the flow cytometric FITC-Annexin V binding assay.

Changes in the plasma membrane of the cell surface are one of the earliest features of cells undergoing apoptosis (Vermes, et al., *J. Immunol Meth* 1995; 184:39–51). In apoptotic cells, the membrane phospholipid phosphatidyl serine is translocated from the inner to the outer leaflet of the plasma membrane, thereby exposing phosphatidyl serine to the external cellular environment (Martin, et al., *J Exp Med* 1995; 182:1545–1556). Annexin V binds to phosphatidyl serine residues which are exposed on the surface of cells undergoing apoptosis. As shown in FIG. 8, VDC-treated sperm showed a time-dependent increase in binding of Annexin V which was evident at 2 hours and reached a maximum by 12 hours. Nearly 60% of VDC-treated sperm were apoptotic by 12 hours of incubation. Hydrogen peroxide ($H_2O_2$; 8 mM), which was used as positive control agent, also induced apoptosis. $H_2O_2$-induced apoptosis was evident at 2 hours and reached a maximum at 4 hours (FIG. 8). Control sperm treated with 0.1% DMSO alone showed <10% apoptosis at all time points.

C. Analysis of Apoptosis Using DNA Nick End Labeling by TUNEL Method

A flow cytometric two-color terminal dideoxynucleotidyl transferase (TdT) assay was employed to detect apoptotic sperm nuclei by DNA nick end labeling (TUNEL; Gavrieli, et al., *J Cell Biol* 1992; 119:493–501). Motile human sperm ($5 \times 10^6$/ml) were incubated in DMSO alone (0.1%) or treated with 100 μM of VDC in 0.1% DMSO or 8 mM $H_2O_2$ for 0, 1, 2, 4, 8, 12, 24 and 48 hours. Sperm were washed in phosphate buffered saline (PBS), fixed in 1% paraformaldehyde in PBS for 15 minutes on ice. Following two washings in PBS, they were permeabilized with 70% cold ethanol and stored at −20° C. for <2 days. New 3'-hydroxyl (3'—OH) end labeling of fragmented sperm nuclear DNA was performed using TdT and digoxigenin-conjugated Uridine Triphosphate (UTP) followed by immunodetection of the incorporated dUTP using the ApopTag in situ apoptosis detection kit according to the manufacturer's recommendations (Oncor, Gaithersburg, MD). Non-apoptotic cells do not incorporate significant amounts of dUTP due to lack of exposed 3'—OH ends, and consequently have relatively little fluorescence compared to apoptotic cells which have an abundance of 3'—OH (M2 gates). VDC-induced apoptosis is shown by an increase in the number of cells staining with anti-digoxigenin-FITC monoclonal antibody (M2 gates). The M1 and M2 gates were used to demarcate non-apoptotic and apoptotic PI-counterstained sperm populations, respectively. Two separate experiments were performed in duplicate to assess dUTP incorporation following exposure of sperm to VDC and $H_2O_2$.

In studies to evaluate the comparative effect of 4 vanadocene dihalides (VDB, VDC, VMDC, and VDI) and 5 vanadocene di-pseudohalides (VDA, VDCN, VDOCN, VDSCN, and VDSeCN) and 3 vanadocene disubstituted derivatives (VDT, VDCO, and VDFe) to induce apoptosis, 1 ml aliquots of motile sperm ($10^7$/ml) in triplicate were incubated in BWW-0.3% BSA at 37° C. for 24 hours with and without 100 μM each of the test compounds. Sperm incubated with 8 mM $H_2O_2$ served as a positive control. The apoptotic sperm nuclei were quantitated by TdT-mediated dUTP-digoxigenin nick end labeling method, as described above. Sperm aliquots incubated without TdT enzyme served as a negative control.

RESULTS
D. Apoptosis Shown by DNA-Nick End Labeling

Figure 9A:
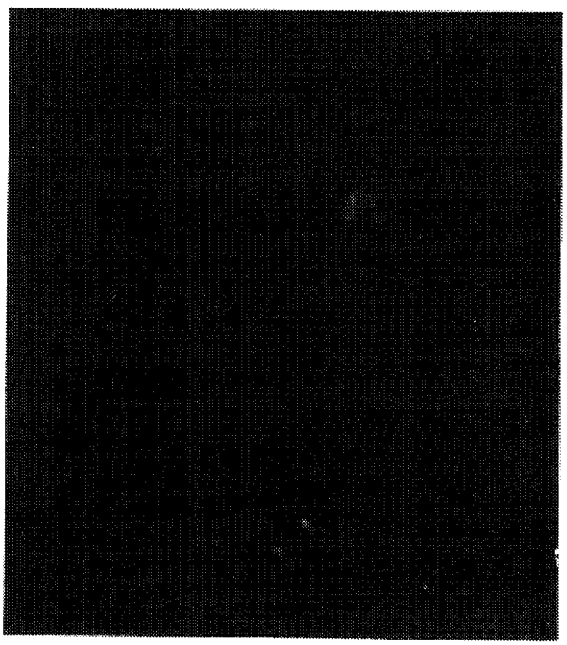
FIG. 9 are confocal laser scanning microscopy images of apoptotic nuclei in VDC-treated sperm.
Figure 9B:
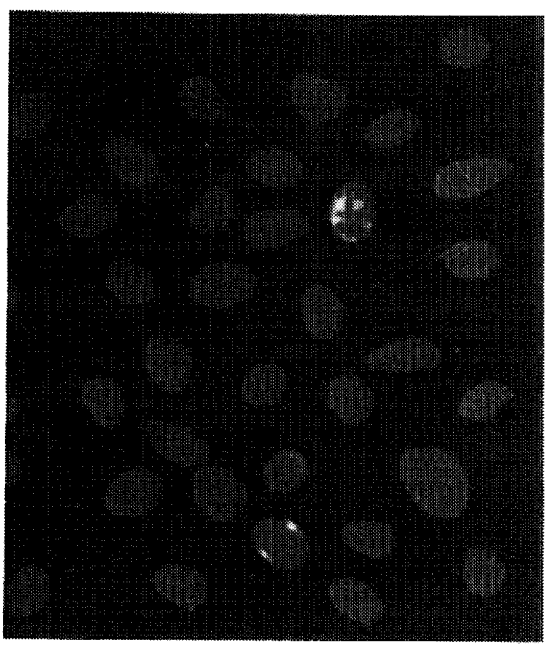
Figure 9C:
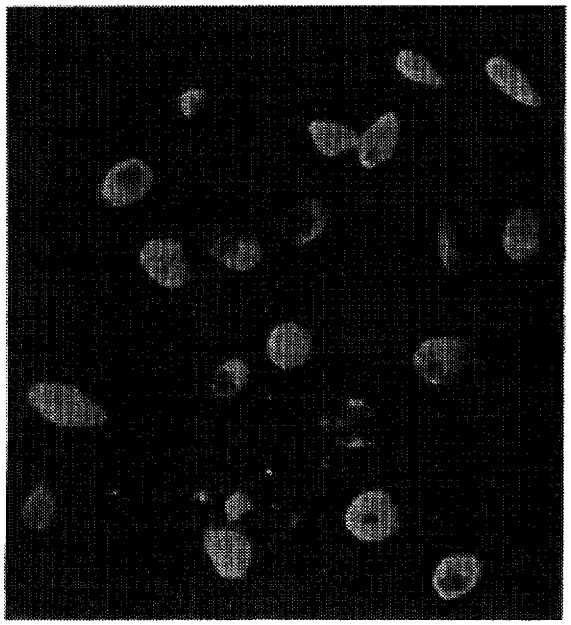
Figure 9D:
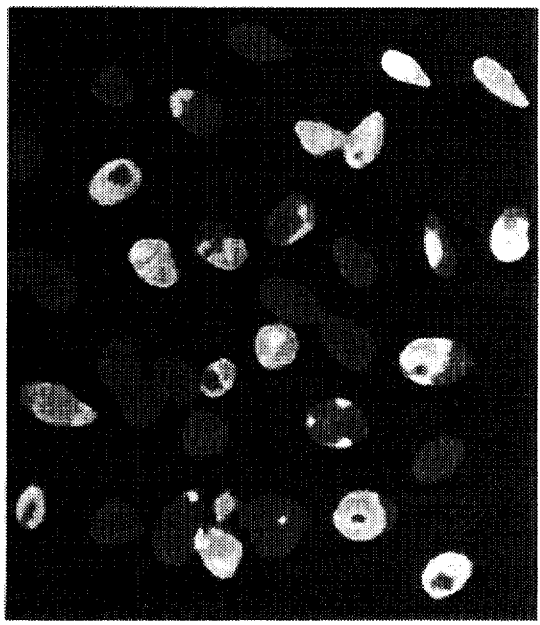
Figure 10:
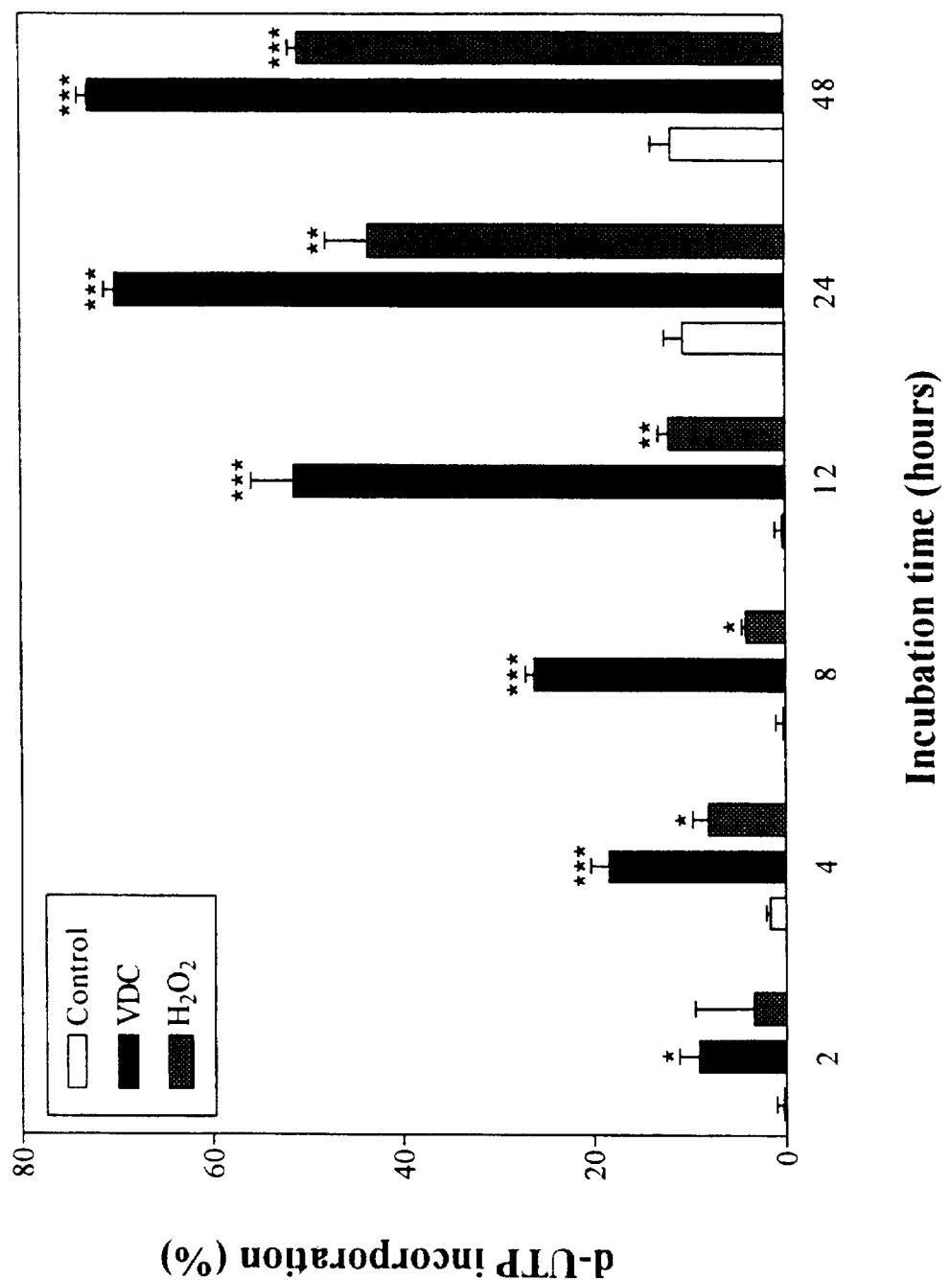
FIG. 10 is a bar graph illustrating time-course of sperm labeling by TUNEL method following treatment with VDC.

The TdT-mediated labeling of 3'—OH termini with digoxigenin-conjugated UTP by the in situ TUNEL method was used to confirm that VDC induces apoptosis in human sperm. FIGS. 9A–C depict the two-color confocal microscopy images of sperm nuclei of control sperm treated with 0.1% DMSO (FIG. 9A), and test sperm treated with 100 μM VDC in 0.1% DMSO after staining with digoxigenin-conjugated dUTP followed by immunodetection of the incorporated dUTP with anti-digoxigenin-FITC monoclonal antibody with (right panels; A2 and B2) and without (left panels; A1 and B1) PI-counterstaining. Nuclei of VDC-treated sperm showed dual fluorescence, due to the abundance of 3'-hydroxyl end labeling of fragmented sperm nuclear DNA, consistent with apoptosis. A time-dependent increase of apoptotic sperm nuclei was observed after VDC treatment (FIG. 10). The VDC-induced dUTP incorporation, which was evident at 2 hours after exposure to 100 μM VDC in 0.1% DMSO, reached a maximum of 70.0%±1.1% by 24 hours. By contrast, <10% of control sperm treated with 0.1% DMSO became apoptotic after 24 hours of incubation. The extent of dUTP incorporation by VDC was consistently greater than that induced by $H_2O_2$ which was used as a positive control (70.0%±1.1% vs 43.5%±4.5%; p<0.05).

Example III

Effect of Deferoxamine on Spermicidal Activity of VDC

In order to study the effects of deferoxamine (Sigma Chemical Co.) on VDC-induced spermicidal activity, 1 ml aliquots of motile sperm ($10^7$/ml) in BWW-0.3% BSA were incubated at 37° C. for 3 hours in the presence and absence of 50 μM VDC and increasing concentrations of deferoxamine (2.5, 5.0 and 10 mM). Following incubation, 4 μl aliquots were transferred to 20 μm Microcell chambers and sperm motility was assessed by CASA, as described above. The motilities and kinematic parameters of sperm were compared to those of sperm suspensions from similarly processed controls. Three separate experiments were performed to test the protective effect of deferoxamine on VDC-induced sperm motility loss.

A. Deferoxamine Protects Against Vanadocene

Figure 5A:
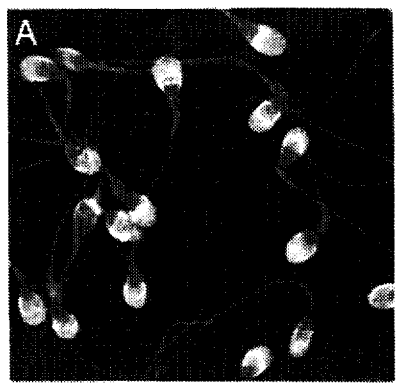
FIG. 5 shows laser scanning confocal fluorescence images of sperm.
Figure 5B:
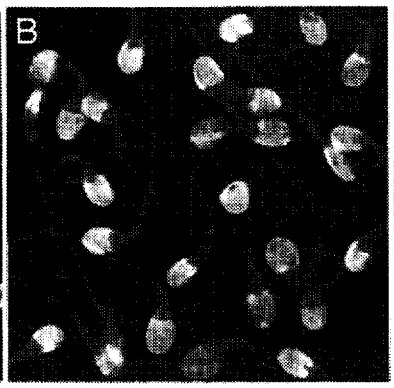
Figure 5C:
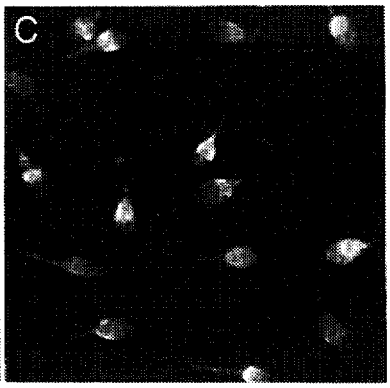

Deferoxamine has been shown to be an efficient vanadium chelator. As shown below in Table 1, coincubation of motile sperm with 50 μM VDC and increasing concentrations of deferoxamine (2.5–10 mM) resulted in dose-dependent protection of sperm motility and sperm motion parameters, as assessed by CASA. A 3 hour coincubation of VDC with deferoxamine at a molar ratio of 1:50 to 1:200 resulted in 62% to 85% retention of sperm motility. The mean values of the other sperm movement characteristics (VCL, VAP, VSL, STR, LIN, BCF, and ALH) also showed >80% protection of VDC-treated sperm at a 1:200 molar ratio of VDC:deferoxamine. There were no significant differences in these parameters between untreated control and VDC:deferoxamine (molar ratio of 1:200) treated sperm ($p>0.15$). A dose-dependent increase in mean progressive motility was one of the most conspicuous effect of deferoxamine in VDC-treated sperm.

the sperm heads exhibited a uniform, bright green fluorescence (FIG. 5). In acrosome-reacted sperm, green fluorescence was either absent or restricted to the equatorial segment of the sperm heads. Again, sperm exposed to 100 μM VDC did not reveal an increased acrosome reaction after 3 hours of incubation (FIG. 5). In contrast, sperm exposed to 100 μM nonoxynol-9 for 3 hours under identical conditions revealed complete loss of acrosomal staining (FIG. 5).

Figure 6A:
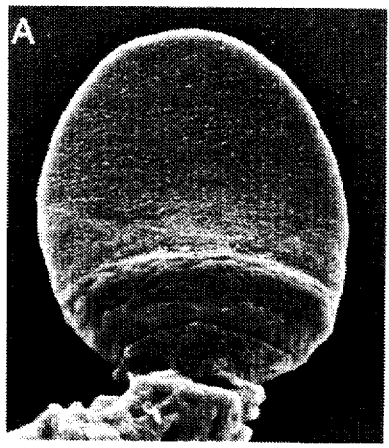
FIGS. 6A and 6B show a high-resolution low-voltage SEM of sperm incubated in the absence (FIG. 6A) and presence of 100 µM VDC (FIG. 6B) or 10 µM Ca-Ionophore (FIG. 6C) after 3 hours of treatment (×18,000 magnification).
Figure 6B:
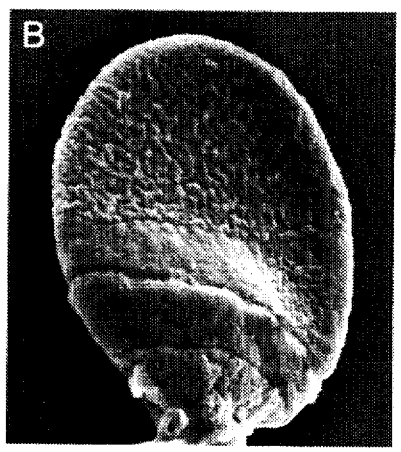
Figure 6C:
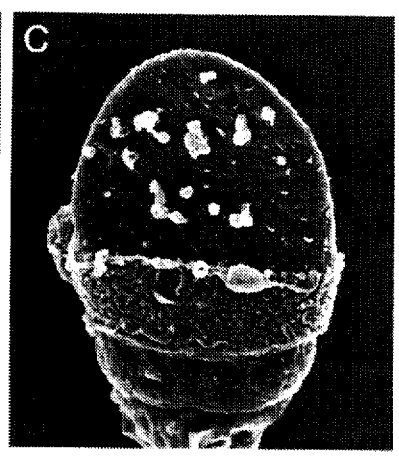

Examination of by HR-LVSEM confirmed that acrosomes of VDC (100 μM for 3 hours)-treated sperm remained intact, as they were clearly discernible from the smooth post-acrosomal regions (FIG. 6B). When compared with control sperm (FIG. 6A), VDC-treated sperm showed signs of mild membrane ruffling of the acrosomal region of sperm head. By contrast, CaI-treated sperm revealed characteristic blebbing or vesiculation, fenestration, and loss of the plasma and acrosomal membranes (FIG. 6C).

C. pH-Optimum for Spermicidal Activity

Metallocene complexes have been shown to be less stable in alkaline solutions because of pH-dependent dissociation subsequent and hydrolysis reactions (Toney, et al., *J Am*

TABLE 1

Protective effect of deferoxamine (DFO) on the movement characteristics of VDC-treated sperm

| Treatment | Motility (%) | Progressive Motility (%) | VCL (μm/sec) | VAP (μm/sec) | VSL (μm/sec) | STR (%) | LIN (%) | BCF (Hz) | ALH (μm) |
|---|---|---|---|---|---|---|---|---|---|
| Control | 81.6 ± 14.7 | 48.0 ± 20.3 | 96.0 ± 15.1 | 57.6 ± 11.8 | 48.3 ± 12.0 | 81.6 ± 5.0 | 50.0 ± 6.5 | 22.7 ± 1.7 | 5.0 ± 0.4 |
| VDC (50 μM) | 0 | 0 | 0 | 0 | 0 | 0 | 0 | 0 | 0 |
| VDC (50 μM) + 2.5 mM DFO | 50.3 ± 22.1 | 16.6 ± 11.4 | 59.9 ± 11.6 | 37.9 ± 10.5 | 31.9 ± 11.0 | 80.3 ± 6.0 | 50.6 ± 8.2 | 26.7 ± 1.5 | 3.4 ± 0.3 |
| VDC (50 μM) + 5 mM DFO | 57.3 ± 22.5 | 29.0 ± 17.5 | 72.7 ± 7.5 | 45.4 ± 8.6 | 39.3 ± 9.3 | 83.3 ± 4.5 | 51.6 ± 7.1 | 25.0 ± 3.7 | 3.8 ± 0.2 |
| VDC (50 μM) + 10 mM DFO | 69.6 ± 15.4 | 38.6 ± 20.0 | 77.0 ± 6.2 | 50.0 ± 8.1 | 44.0 ± 9.1 | 85.0 ± 4.2 | 55.3 ± 8.0 | 21.0 ± 3.3 | 3.9 ± 0.4 |

VCL, curvilinear velocity; VAP, path velocity; VSL, straight-line velocity; STR, VSL/VAP; LIN, VSL/VCL; BCF, beat cross frequency; ALH, lateral head displacement. Values are mean ± SD of 3 separate experiments.

B. Vanadocene Spermicidal Activity Does Not Damage Plasma Membrane

Figure 4:
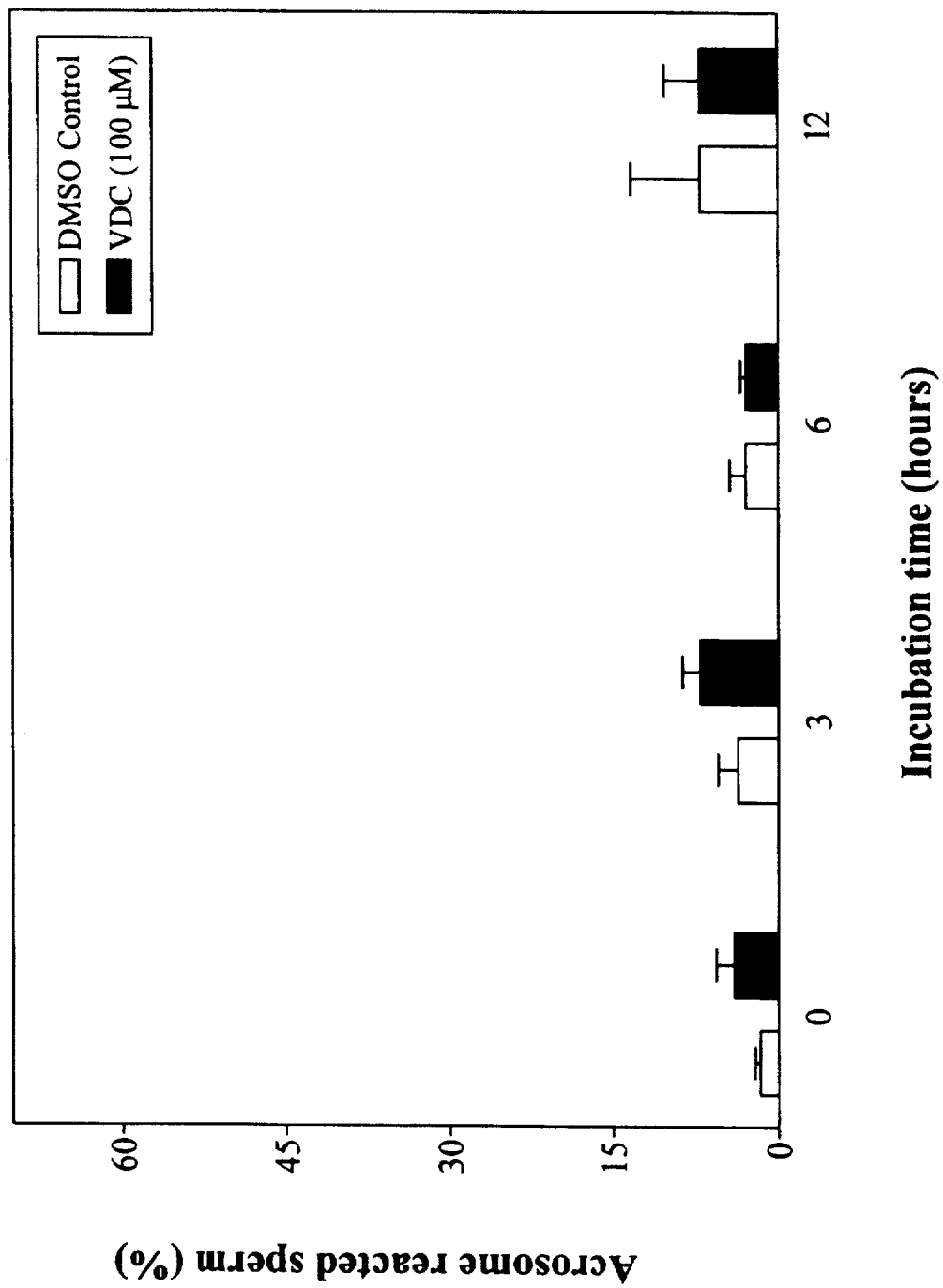
FIG. 4 shows the effect of vanadocene dichloride on sperm acrosomal membrane integrity.

Because the currently used spermicidal compounds are believed to immobilize sperm as a result of a detergent-type action on the sperm plasma membrane, we also tested the effects of VDC on sperm acrosome integrity. Similar to sham-treated sperm, the majority (93%±2.9%) of VDC-treated sperm remained acrosome-intact after 3 hours incubation at 100 μM, despite a complete loss of motility. The percentages of acrosome-reacted sperm after 3, 6, and 12 hours incubation with 0.1% DMSO versus VDC in 0.1% DMSO were 3.7%±1.7% vs 7.0%±1.6%, 3.0%±1.4% vs 3.0%±0.5%, and 7.0%±6.3% vs 7.0%±3.2%, respectively. These results demonstrate that the spermicidal effect of VDC did not result in disruption of the sperm plasma membrane within the acrosomal region of the sperm head (FIG. 4) as would be caused by a detergent-type action. Notably, after 24 hours treatment with 100 μM VDC, the percentage of acrosome-reacted sperm was significantly higher than in controls (58.4%±6.0% vs 5.4%±2.0%; $p<0.05$), indicating the sperm plasma membrane remained intact.

Examination of FITC-lectin, TOTO-3, and Nile red-stained sperm by confocal laser scanning microscopy revealed an intense acrosomal staining (bright green) with FITC-lectin, nuclear staining (blue) with TOTO-3, and plasma membrane staining (red) with Nile-red, respectively. In non-acrosome-reacted sperm, the acrosomal regions of

Figure 7:
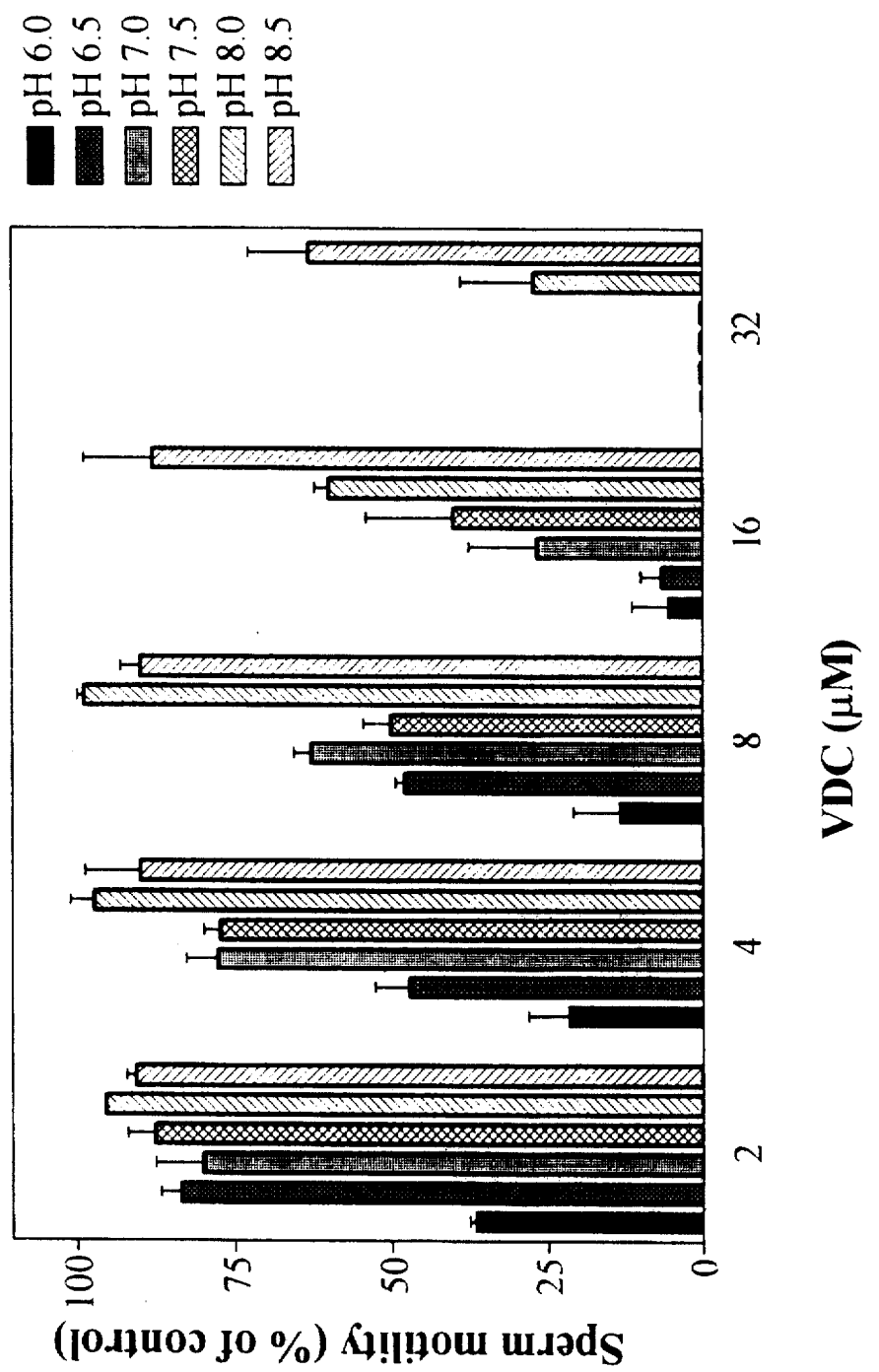
FIG. 7 is a bar graph illustrating the effect of pH on spermicidal activity of VDC.

*Chem Soc* 1985; 107:947–953 and McLauglin, et al., *J Am Chem Soc* 1990; 112:8949–8952). Therefore, we next examined the pH-optimum for the spermicidal activity of VDC. Sperm motility assays using CASA were performed in BWW-0.3% BSA containing 0, 2, 4, 8, 16 or 32 μM of VDC at pH values ranging from 6.0 to 8.5. As shown in FIG. 7, the spermicidal activity of VDC was attenuated by increasing the pH value. At a concentration of 32 μM, VDC induced complete sperm immobilization at pH values ranging between 6.0 and 7.5, whereas it caused only partial sperm immobilization at higher pH values (73%±11% at pH 8.0 and 37%±9.7% at pH 8.5).

D. Irreversibility

In order to determine whether the VDC-induced sperm immobilization was reversible, aliquots of semen or motile fraction of sperm in assay medium were briefly exposed to 100 μM VDC for 15 and 30 seconds. Following immediate dilution, washing, and resuspension in assay medium, sperm motility was reassessed by CASA. Washing of sperm after 15 or 30 seconds of preincubation with 100 μM VDC, which induced complete sperm motility loss, did not result in recovery of sperm motility after resuspension in fresh assay medium (Table 2). Thus, the VDC-induced sperm immobilization was irreversible.

TABLE 2

Effect of brief exposure and sperm washing on VDC-induced sperm immobilizing activity

| Treatment | % Motility[a] | |
|---|---|---|
| | Semen[b] | Percoll fraction[b] |
| DMSO (0.1%) | | |
| 15 seconds | 79 ± 6[c] | 94 ± 2 |
| 30 seconds | 82 ± 4 | 92 ± 3 |
| VDC (100 μM) | | |
| 15 seconds | 0 | 0 |
| 30 seconds | 0 | 0 |

[a]Sperm motility was assessed by CASA.
[b]CASA was performed after 15 minutes of incubation in BWW-0.3% BSA medium without DMSO or VDC
[c]Values are means ± SD of 2 separate experiments

Example IV

Spermicidal Activity of Vanadocene Dihalides and Vanadocene Di-Pseudohalides After establishing the importance of vanadium IV for the spermicidal activity of metallocene dichlorides, several structurally distinct organometallic complexes containing vanadium(IV) were examined from spermicidal activity. These vanadocene complexes included: vanadocene dichloride (VDC), Bis(methylcyclopentadienyl) vanadium dichloride (VMDC), vanadocene dibromide (VDB), vanadocene diiodide (VDI), vanadocene diazide (VDA), vanadocene dicyanide (VDCN), vanadocene dioxycyanate (VDOCN), vanadocene dithiocyanate (VDSCN), vanadocene diselenocyanate (VDSeCN), vanadocene ditriflate (VDT), vanadocene monochloro oxycyanate (VDCO) and vanadocene monochloro acetonitrilo tetrachloro ferrate (VDFe) tested side-by-side and at 11 different concentrations (61 nM to 62.5 μM) for spermicidal activity using CASA.

All of the 4 vanadocene dihalides, 5 vanadocene di-pseudohalides, and 3 vanadocene disubstituted derivatives with various substituents covalently coordinated as ligands to the central metal vanadium (IV) induced a dose-dependent loss of sperm motility (FIGS. 11A and B). Complete loss of sperm motility was achieved with each of the compounds at concentrations <62.5 μM, but marked differences were noted in their potency. Among the 4 vanadocene dihalides tested, VDB (6.1 μM) was the most potent, whereas among the 5 vanadocene di-pseudohalides tested, VDSeCN (0.16 μM) was the most potent. The 3 disubstituted derivatives of vanadocene, VDT, VDCO, and VDFe were equally (20.1–24.4 μM) spermicidal. The concentrations of VDC, VMDC, VDB, VDI, VDA, VDCN, VDOCN, VDSCN, VDSeCN, VDT, VDCO, and VDFe that inhibited sperm motility by 50% (i.e., $EC_{50}$ values) were 9.6 μM, 7.0 μM, 6.1 μM, 17.7 μM, 8.7 μM, 7.2 μM, 9.9 μM, 1.4 μM, 0.16 μM, 20.1 μM, 24.4 μM, and 21.2 μM, respectively. These differences in potency of the spermicidal activity elicited by various vanadocene complexes suggest that, in addition to the central metal vanadium IV, the two other coordinated diacido groups also contribute to their spermicidal activity.

Sperm immobilization by the various vanadocene complexes was very rapid. Within 20 seconds after addition of any of the vanadocene complexes at a final concentration of 200 μM to either highly motile fraction of pooled donor sperm or to aliquots of 1:1 diluted semen as targets, greater than 90% of the previously motile sperm became immotile; after 30–60 seconds of exposure, complete loss of sperm motility was evident as assessed by CASA (data not shown). The time required for sperm immobilization by vanadocene complexes in diluted semen was unaffected by the presence of seminal plasma components. Notably, a 12 hour and 24 hour exposure of motile sperm to 100 μM each of the 12 distinct diacido vanadocene complexes resulted in apoptosis, as measured by the flow cytometric Annexin V binding assay and DNA nick end labeling by the TUNEL method, confirming the irreversible nature of their spermicidal activity (Table 3).

TABLE 3

Flow cytometric quantitation of apoptotic sperm detected by FITC Annexin V binding and in situ DNA nick end labeling of vanadocene exposed sperm

| Treatment | Annexin V-positive sperm[a] (%) | Apoptotic sperm nuclei[b] (%) |
|---|---|---|
| None | 10.7 ± 0.1[c] | 8.35 ± 0.9[d] |
| *Vanadocene halides* | | |
| VDB | 84.3 ± 1.5 | 78.6 ± 2.4 |
| VDC | 85.8 ± 0.8 | 90.6 ± 0.4 |
| VMDC | 77.1 ± 5.2 | 34.4 ± 2.4 |
| VDI | 78.7 ± 0.6 | 94.6 ± 1.3 |
| *Vanadocene di-pseudohalides* | | |
| VDA | 85.9 ± 0.5 | 91.4 ± 2.1 |
| VDCN | 62.1 ± 5.1 | 18.7 ± 2.5 |
| VDOCN | 81.8 ± 1.2 | 92.6 ± 0.5 |
| VDSCN | 63.7 ± 1.1 | 29.0 ± 8.5 |
| VDSeCN | 83.5 ± 0.1 | 82.3 ± 2.6 |
| *Vanadocene disubstituted derivatives* | | |
| VDT | 87.0 ± 0.5 | 87.4 ± 9.4 |
| VDCO | 71.9 ± 3.0 | 52.8 ± 2.4 |
| VDFe | 15.7 ± 0.2 | 60.0 ± 1.2 |

[a]Motile sperm were incubated for 12 hours in either control medium, or in medium supplemented with 100 μM each of the 12 vanadocene complexes, and stained with FITC-conjugated human recombinant Annexin V. Sperm nuclei were counter stained with PI and analyzed by flow cytometry.
[b]Motile sperm were incubated for 24 hours in either control medium, or in medium supplemented with 100 μM each of the 12 vanadocene complexes, fixed, permeabilized, and stained with digoxigenin-dUTP labeling fluorescein kit. Sperm nuclei were counter stained with PI and analyzed by flow cytometry.
[c]Data are mean ± SD of duplicate assessments.
[d]Data are mean ± SD of two experiments.

Figure 12:
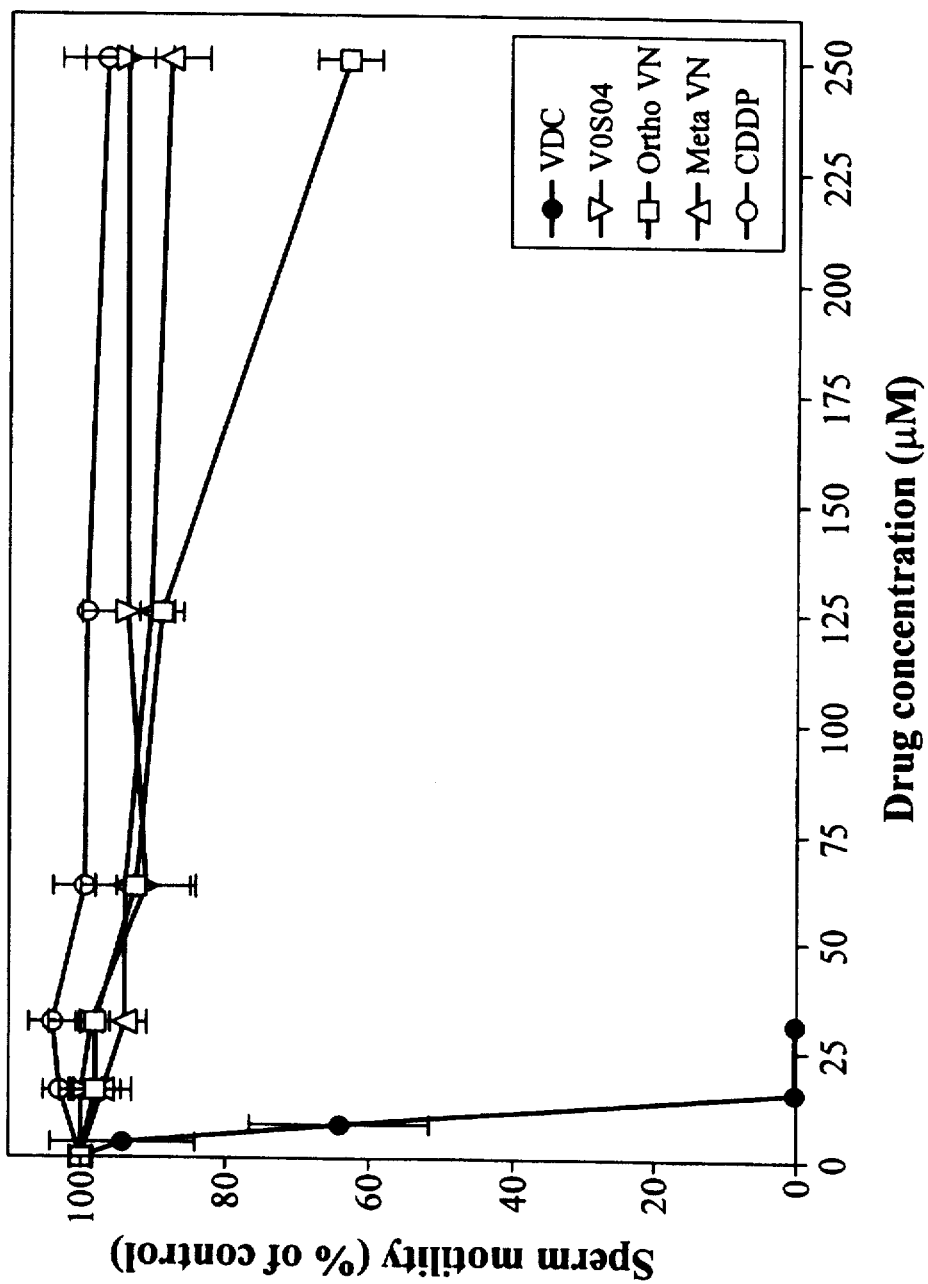
FIG. 12 is a graph shoving dose response for inorganic vanadium compounds, and indicating lack of spermicidal activity by these compounds.

The potential spermicidal effects of vanadyl (vanadium [IV]) sulfate, sodium orthovanadate (V), and sodium metavanadate (V) were also tested at the same concentrations. In sharp contrast to the organometallic compounds containing vanadium (IV), inorganic salts of vanadium (oxidation state IV and V) lacked spermicidal activity even at 250 μM and orthovanadate showed only a 37% reduction in sperm motility at the highest concentration tested (FIG. 12). Similarly, the inorganic platinum complex, cis-diamminedichloroplatinum(II) (cis-$(NH_3)_2PtCL_2$=cisplatin) did not affect sperm motility.

Example V

Spermicidal Activity of Chelate Complexes of Vanadocene Derivatives

Figure 13:
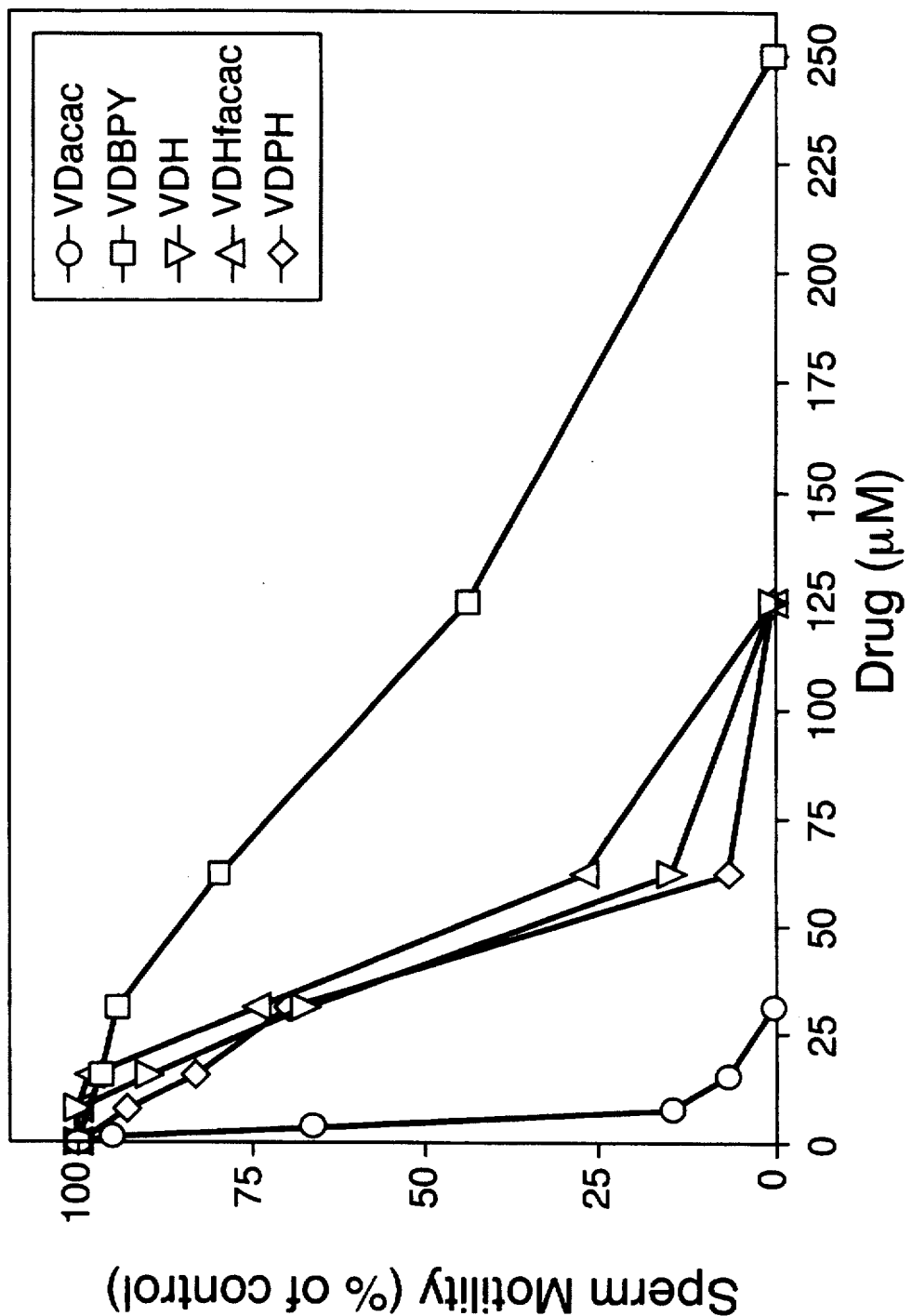
FIG. 13 is a graph showing dose response curves for five chelated complexes of vanadocene derivatives on sperm motility, including VDacac, VDBPY, VDH, VDHfacac and VDPH.

The comparative spermicidal activities of five chelated vanadocene derivatives, VDacac, VDBPY, VDHfacac, VDH, and VDPH were tested at the same concentrations, using the methods and procedures described above for Example IV. All of these five blocked vanadocenes exhibited spermicidal activity at micromolar concentrations. [FIG. 13] However, these vanadocenes showed 7.2 to 22.5-fold differences in their potency. The concentrations of each compound that inhibited sperm motility by 50% are shown below. In addition, apoptosis induced by these agents using the methods described above for Example IV is quantitated in the table below. The data indicate that VDacac was most potent, while VDBPY was least active. These differences in spermicidal activity of the chelated vanadocenes further confirms that, in addition to the central metal vanadium IV, chelation of the bidentate functional groups also contributes to the spermicidal properties of these compounds.

| VDacac | VDBPY | VDHfacac | VDH | VDPH |
|---|---|---|---|---|
| 4.7 μM | 106 μM | 45.5 μM | 37.6 μM | 34 μM |

| Treatment | Annexin - V-Positive Sperm % | Apoptotic Sperm Nuclei % |
|---|---|---|
| None Vanadocene Chelate Complexes | 9.6 ± 0.3 | 3.9 ± 2.8$^d$ |
| VDacac | 91.6 ± 1.2 | 84.0 ± 5.6 |
| VDBPY | 19.3 ± 2.2 | 11.0 ± 1.3 |
| VDH | 39.2 ± 5.4 | 26.1 ± 4.6 |
| VDPH | 65.2 ± 2.2 | 93.0 ± 5.0 |
| VDHfacac | 86.0 ± 0.8 | 96.9 ± 0.4 |

DISCUSSION OF RESULTS

The above results provide evidence that vanadium-containing metallocene complexes have potent and irreversible spermicidal activity against human sperm. Computer-assisted sperm analysis revealed that the observed spermicidal activity of the vanadocene complexes such as vanadocene dichloride (VDC) was proportional to their effects on the track speed (VCL), path velocity (VAP), and straight line velocity (VSL) of sperm. With the most potent metallocene complexes described herein, sperm motility loss was complete within less than 1 minute.

Non-vanadium metallocene complexes containing hafnodium, molybdenum, titanium or zirconium containing metal had minimal effects on sperm motility. Thus, the spermicidal activity of vanadocene complexes was dependent on vanadium as the central metal atom. Furthermore, substitution of the dichloride group of VDC with either bromide, azide, cyanide, selenocyanate, or thiocyanate resulted in further increase in spermicidal activity. In particular, di-pseudohalide substitutions with thiocyanate (SCN) and selenocyanate (VDSeCN) appeared to increase the spermicidal potency of vanadocene complexes by nearly 7 to 60-fold when compared with the prototype vanadocene dichloride VDC. The order of efficacy was VDSeCN>VDSCN>VDB>VMDC>VDCN>VDA>VDC>VDOCN>VDI>VDT>VDFe>VDCO. VDSeCN and VDSCN were spermicidal at nanomolar concentrations.

In addition, chelation of the bidentate functional moiety in the vanadocene coordination sphere resulted in both an increase and decrease in spermicidal activity. Among the five chelated vanadocenes evaluated, the spermicidal activity of VDacac was similar to that of VDC. The order of efficacy was VDacac>VDC>VDHfacac>VDPH>VDH>VDBPY.

Whereas a very short exposure to vanadocene complexes at nanomolar-micromolar concentrations was sufficient to induce sperm motility loss, prolonged exposure of membrane-intact live sperm to mM concentrations of inorganic vanadium salts, such as vanadyl sulfate (IV) and sodium metavanadate, had no effect on motility of membrane-intact sperm. These results are consistent with a previous report showing that inorganic vanadium compounds in the [+V] oxidation state, such as sodium metavanadate and sodium orthovanadate, inhibit sea urchin sperm motility only following demembranation of the sperm (Gibbons, et al., Proc Natl Acad Sci USA 1978; 75:2220–2224). Similarly, the inorganic platinum complex, cis-diamminedichloro-platinum(II) (cisplatin) did not elicit any spermicidal activity.

The findings that the acrosome structure of VDC-immobilized sperm remains intact even after 12 hours of exposure demonstrated that the vanadocene metallocomplex-induced immobilization of human sperm is not mediated by membrane disruption. In this regard, vanadocene complexes differ from the aforementioned detergent-type vaginal spermicides. Since vanadocene complexes do not immobilize sperm by a direct detergent-type action on sperm membranes, their potent spermicidal activity holds particular clinical promise and recommends their further development as a new class of vaginal contraceptives.

VDC, as well as other vanadocene diacido complexes, tested side-by-side induced apoptosis of human sperm, as shown by increased FITC-Annexin V binding to sperm surface and increased dUTP incorporation into sperm DNA. Confocal microscopy images confirmed the results of dUTP incorporation in the nuclei of VDC-treated sperm. We attribute the irreversible nature of the spermicidal activity of VDC to its ability to induce apoptosis.

Example VI

Contraceptive Effect in Test Animals

Physiological fertilization is dependent on successful sperm transport in the female genital tract. The requirement of detergent-type activity of commercial vaginal contraceptives to inhibit sperm transport in the female genital tract has been shown to cause lesions and severe ulceration of vaginal epithelium in laboratory animals (Tryphonas et al., 1986, Toxicol. 39:177–186; Tryphonas et al., 1984 Toxicol Lett 20:289–295) and vaginal irritation in women (Niruthisard et al., 1991 Sex. Transm. Dis. 18:176–179). Damage to the cervicovaginal epithelium of this sort could lower resistance to sexually transmitted diseases (STDs), including human immunodeficiency virus (HIV). The in vitro studies described above have demonstrated that vanadium IV-containing vanadocenes are potent spermicidal agents and do not induce membrane disruption as do known commercial vaginal spermicides. The lack of membrane damage in the presence of spermicidal vanadocenes suggests the possibility that these spermicides may be useful clinically as a new class of vaginal contraceptives.

The efficacy of the spermicidal vanadocenes as the active ingredient of a vaginal contraceptive for use in mammals is tested in small animal models. Specifically, the effectiveness of precoital intravaginal administration of spermicidal vanadocenes (about 0.025% w/v), for example in a vaginal cream, is evaluated, measuring various reproductive functions including inhibition of sperm transport, fertilizing capacity, and fertility outcome. The effect of the compounds on gametes, embryos, and tissues of the genital tract are also evaluated.

Suitable animal models include Swiss mice and New Zealand rabbits. These animals are particularly suited for these studies because of their relatively short gestation time (19 and 31 days respectively), the ease with which the females can be superovulated, and the ability to perform longitudinal fertility and toxicity studies. Moreover, the reproductive physiology of these animals has been well documented in the literature.

For the fertility trials, at least 24 female mice and 8 female rabbits per experimental group are used. Gonadotropins are administered to sexually mature virgin females to induce superovulation. The vanadocene formulation (0.025% w/v) is administered to the hormonally primed females, intravaginally. The females are subsequently mated with proven breeder males or artificially inseminated with either ejaculated or epididymal preparations of sperm and allowed to complete any pregnancy. The litter size, weight, sex ratio, fetal length, and condition of any offspring at birth is recorded. The in vivo spermicidal effect of vanadocenes versus a detergent spermicide, for example nonoxynol-9, is assessed by comparing the level of pregnancy reduction achieved in comparison with controls, as well as the consistency of the response.

An alternative measure for the fertility outcome is the number of fertilized eggs which undergo cleavage 36 hours after mating, or the number of embryos in uteri after 8 days of gestation. For these studies, females are dissected to expose the uteri and the number of implantation and resorption sites are recorded. The efficacy of the vanadocenes, and particularly of the preferred compounds, VDC, VDSeCN, and VDPH, to reduce fertility is compared with nonoxynol-9 or other known spermicidal agent. All the fertility comparisons are based on the total number of pregnancies, i.e., the percentage of females pregnant after each treatment and mating, and the average litter size. These values are statistically analyzed.

In addition to the fertility studies, a side-by-side comparison of the local toxicity of the spermicidal compounds of the invention with other known spermicidal agents, such as nonoxynol-9 is made following repetitive intravaginal application of the spermicidal compounds to test animals. For example, mice, in subgroups of 10, are administered the agent for up to 30 consecutive days. Following exposure of the female genital tract to these compounds, the females are sacrificed and the genital tract is processed for histopathology and immunohistochemical studies to determine the extent of local inflammatory response.

Example VII

Vanadocene Complexes Induce Apoptosis of Male Germ Cells in vivo

The experiments discussed above demonstrates vanadocenes as effective spermicidal and apoptosis-inducing agents. These properties also extend to the use of the vanadocene complexes as agents to induce selective destruction of mammalian testicular germ cells through apoptosis. Selective destruction of testicular germ cells is useful, for example, for in vivo selective killing of testicular germ cell tumors as well as selective killing of normal mammalian germ cells (chemical castration).

To investigate the ability of the vanadocenes to induce germ cell apoptosis in vivo, these compounds were administered to adult male mice during the germ cell maturation period. Proven breeder adult male CD-1 mice (Charles River Laboratories, Wilmington, MA) 5–6 months of age and weighing about 35 g were used in this study.

Each treatment group (n=5) received bilateral testicular injections of 0.05 ml of vehicle or vanadocene complex (VDA, VDCN, VDCO, or VDOCN) dissolved in 10% DMSO in saline to deliver a dose of 15 mg/kg body weight to each testis. The composition was administered on alternate days for a 28-day period, a total of 14 injection days.

After the twenty-eight day period, the mice were killed by cervical dislocation, and the reproductive tracts were dissected to obtain cauda epididymides and testes. Testes from each animal were weighed, and one testis from each mouse was fixed in 10% buffered formalin for histological analysis.

To detect germ cell apoptosis, conventional paraffin-embedded sections (6 μm) were prepared from each testis and stained with hematoxylin and eosin. The prepared slides were viewed under 300× magnification with a Leica microscope interfaced with an image analysis system, and the images transferred to Adobe Photoshop™ software for printing.

The degree of spermatogenesis and the stages of the germinal epithelia were determined histologically. The terminal deoxynucleotidyl transferase-mediated dUTP nick end-labeling (TUNEL) method was used for in situ detection of DNA strand breaks in apoptotic cells.

Histological analysis indicated selective loss of germ cells within the seminiferous tubules of VDA, VDCN, VDCO, and VDOCN-exposed testes. The seminiferous tubules exhibited various degrees of degenerative changes including vacuolization, giant cell formation, absence of mature sperm in the lumen, and overall decrease in tubular diameter. The Sertoli cells and interstitial cells were all normal in appearance at the light microscopic level.

Figure 14A:
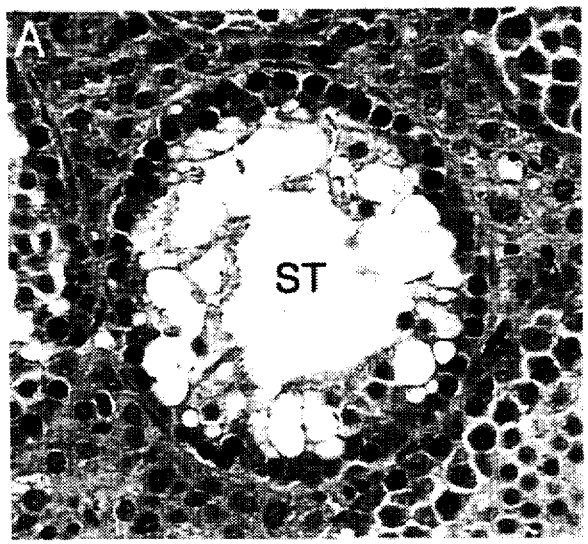
FIGS. 14A and 14B are photographs showing histological analysis of stained sections of adult male mice testis (FIG. 14A) and corresponding confocal laser scanning images of apoptotic cells in the testis detected by the TUNEL method (FIG. 14B) following intratesticular administration of VDCN.
Figure 14B:
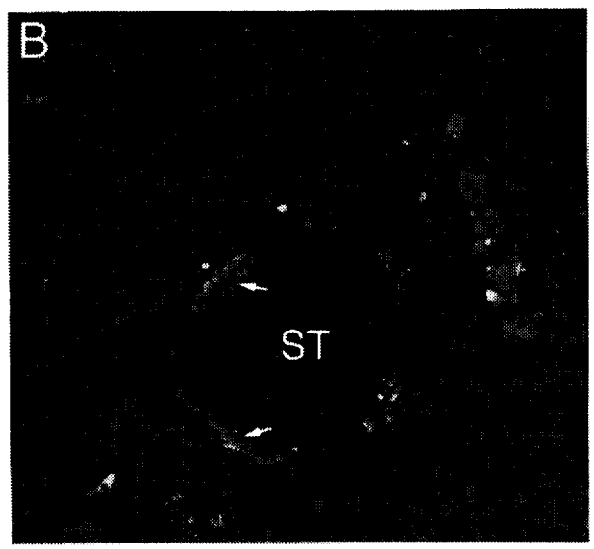

Using in situ detection and confocal microscopy by which apoptotic cells are identified by their bright green fluorescence, less than 5 cells/100 tubules appeared apoptotic in control testis. In contrast, vanadocene-treated testis demonstrated 12–55 apoptotic cells/100 tubules. FIG. 14A shows a tissue section of VDCN-exposed testis with complete loss of germ cells within the seminiferous tubule. FIG. 14B shows residual apoptotic germ cells within the degenerating seminiferous tubule of the VDCN-exposed testis by laser confocal microsopy TUNEL method.

These findings demonstrate that testicular germ cell apoptosis was induced by exposure to vanadocene complexes, in vivo. This activity indicates application of the vanadocene complexes as male antifertility agents and for selective destruction of germ cells, such as in testicular germ cell tumors.

The invention described herein may be modified to include alternative embodiments. All such obvious alternatives are within the spirit and scope of the invention, as claimed below.

What is claimed is:

1. A method of inhibiting motility of sperm comprising contacting sperm with an organometallic cyclopentadienyl vanadium IV complex.

2. The method of claim 1, wherein said organometallic cyclopentadienyl vanadium IV complex is a vanadocene dihalide.

3. The method of claim 2, wherein said vanadocene dihalide is a dichloride.

4. The method of claim 3, wherein said dichloride is bis(methylcyclopentadienyl) vanadium dichloride or vanadocene dichloride.

5. The method of claim 1, wherein the contacting step includes administering the organometallic cyclopentadienyl vanadium IV complex to a patient by injection.

6. The method of claim 1, wherein the contacting step includes administering the organometallic cyclopentadienyl vanadium IV complex to a patient via a prolonged release composition.

7. The method of claim 1, wherein the contacting step includes administering the organometallic cyclopentadienyl vanadium IV complex to a patient via an intravaginal insert.

8. The method of claim 1, wherein the contacting step includes administering the organometallic cyclopentadienyl vanadium IV complex to a patient via a condom.

* * * * *